US00RE49294E

(19) United States
(12) Reissued Patent
Slavcev et al.

(10) Patent Number: US RE49,294 E
(45) **Date of Reissued Patent: *Nov. 15, 2022**

(54) DNA VECTOR PRODUCTION SYSTEM

(71) Applicant: Mediphage Bioceuticals, Inc., Waterloo (CA)

(72) Inventors: Roderick Slavcev, Waterloo (CA); Nafiseh Nafissi, Toronto (CA)

(73) Assignee: Mediphage Bioceuticals, Inc., Toronto (CA)

( * ) Notice: This patent is subject to a terminal disclaimer.

(21) Appl. No.: 16/810,504

(22) Filed: Mar. 5, 2020

Related U.S. Patent Documents

Reissue of:
(64) Patent No.: 9,862,954
Issued: Jan. 9, 2018
Appl. No.: 15/047,029
Filed: Feb. 18, 2016

U.S. Applications:
(63) Continuation of application No. 16/668,950, filed on Oct. 30, 2019, now Pat. No. Re. 48,908, which is an application for the reissue of Pat. No. 9,862,954, which is a continuation-in-part of application No. 14/087,715, filed on Nov. 22, 2013, now Pat. No. 9,290,778.

(60) Provisional application No. 61/729,384, filed on Nov. 22, 2012.

(51) Int. Cl.

| | |
|---|---|
| ***C12N 15/74*** | (2006.01) |
| ***C12N 9/22*** | (2006.01) |
| ***C12P 19/34*** | (2006.01) |
| ***C12N 15/85*** | (2006.01) |
| ***G11B 19/20*** | (2006.01) |
| *C12N 15/11* | (2006.01) |

(52) U.S. Cl.
CPC ..... *C12N 15/74* (2013.01); *C12N 9/22* (2013.01); *C12N 15/85* (2013.01); *C12P 19/34* (2013.01); *C12Y 301/00* (2013.01); *G11B 19/2036* (2013.01); *C12N 15/111* (2013.01); *C12N 2310/20* (2017.05); *C12N 2320/11* (2013.01); *C12N 2330/51* (2013.01); *C12N 2795/10322* (2013.01); *C12N 2800/30* (2013.01); *C12N 2830/002* (2013.01)

(58) Field of Classification Search
CPC ..... C12N 15/11; C12N 15/70; C12N 15/85
See application file for complete search history.

(56) References Cited

U.S. PATENT DOCUMENTS 7,897,380 B2 3/2011 Kay et al.

OTHER PUBLICATIONS

Mizuuchi et al., PNAS, 1980, vol. 77, pp. 3220-3224.
Casjens et al., Journal of Bacteriology, 2004, vol. 186, pp. 1818-1832.
Beltecki et al., Nature Biotechnology, 2003, vol. 21, pp. 321-324.
Kaczmarczyk et al., Nucleic Acids Research, 2001, vol. 29, pp. 1-13.
Nafissi et al., 13th CSPS Annual Meeting, Jun. 2-5, 2010, p. 131 accessed: https://ejournals.library.ualberta.ca/indexphp/php/JPPS/article/viewFile/9191/7317.

*Primary Examiner* — Bruce R Campell
(74) *Attorney, Agent, or Firm* — Sterne, Kessler, Goldstein & Fox P.L.L.C.

(57) ABSTRACT

A vector production system is provided. The system comprises recombinant cells designed to encode at least a first recombinase under the control of an inducible promoter and the cells include an expression vector encoding a nucleic acid of interest within the regulatory elements of the expression vector which are flanked on either side by a target sequence for at least the first recombinase. The vector production system provides an efficient one-step process for producing linear or circular covalently closed vectors that incorporate a nucleic acid sequence of interest.

22 Claims, 12 Drawing Sheets

Specification includes a Sequence Listing.

| | | |
|---|---|---|
| SV40E | 1 | 72 |
| *pal* | 23 | 87 |
| *loxP* | 88 | 120 |
| *FRT* | 121 | 154 |
| *pal* | 169 | 201 |
| *telR1* | 203 | 256 |
| *pal* | 257 | 271 |
| SV40E | 272 | 343 |

B

C

A

| Plasmid Conformation | Integrant Viability |
|---|---|
| Circular (CCC::CAT) | 1.0 |
| Linear (LCC::CAT) | $6.5 \times 10^{-3}$ |

B

DNA VECTOR PRODUCTION SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*More than one reissue application has been filed for the reissue of U.S. Pat. No. 9,862,954. This application is a continuation reissue of U.S. application Ser. No. 16/668,950 (pending), which is an application for reissue of U.S. Pat. No. 9,862,954.*

FIELD OF THE INVENTION

The present invention relates generally to DNA vectors, and in particular to a novel DNA vector and a system for producing such vectors.

*REFERENCE TO SEQUENCE LISTING SUBMITTED ELECTRONICALLY VIA EFS-WEB*

*The content of the electronically submitted sequence listing (Name: 4471_001REI1_Seqlisting_ST25; Size: 4,875 bytes; and Date of Creation: Apr. 15, 2022) is herein incorporated by reference in its entirety.*

BACKGROUND OF THE INVENTION

The utility of any gene therapy strategy is defined by its balance between safety and effectiveness. While virus-derived vectors offer exceptional potential to target and deliver DNA cargo with high efficiency into the target cell, viral strategies often suffer in their safety profiling. Recent viral gene therapy-related patient mortalities in clinical trials highlight some of the safety issues attributed to the use of viral gene transfer systems that include, but are not limited to, unwanted immune responses to viral capsid proteins, regeneration of virulent viruses, and insertional mutagenesis. In contrast, non-viral strategies based on naked, lipoplexed or polyplexed plasmid DNA (pDNA) vectors generally offer safer gene therapy, vaccine design, and drug delivery approaches. Plasmid DNA vectors are relatively easy to generate and store and offer tremendous design capacity.

Several major barriers need to be considered in order to develop non-viral gene delivery systems as a therapeutic product to be safely administered in vivo. A successful transgene delivery system depends on the entrance of the DNA vector into the mammalian host nucleus and expression of the encoded transgene(s). While simple in theory, several cellular barriers must be overcome in practice. Vectors must be bio- and immune-compatible and avoid degradation by serum nucleases and immune detection by phagocytes, while travelling in the extracellular surroundings. Plasma nucleases digest the unprotected DNA within just a few minutes, so DNA vectors need to rapidly cross the plasma membrane of target cells. This is further complicated by the fact that the plasma membrane is composed of dense lipoprotein barriers that intrinsically inhibit efficient DNA translocation. Strategies to overcome this barrier include complexing DNA vectors with synthetic nanoparticles to form a structure similar to the plasma membrane or receptormediated endocytosis; i.e. targeted liposomes. However, while non viral gene delivery techniques work toward efficiency of DNA delivery, they generally prove poor in the delivery of pDNA vectors to the nuclear compartment. Many techniques are currently being investigated to enhance levels of non-viral gene transfer by targeting vectors to the nucleus. These techniques include modification of plasmids with DNA nuclear targeting sequences (DTS), covalent linkage of nuclear localization signals (NLS) to the plasmid DNA constructs, and attachment of import receptors such as karyopherins, to vectors that promote uptake through the nuclear membrane pore complex. Modification of DNA with NLS-conjugates seems to result in highly efficient expression of linear DNA, but not circular DNA, in combination with liposomal delivery vectors. This difference may be attributed to charge per unit ratio of linear versus supercoiled circular DNA and provides yet another intriguing opportunity for lcc vectors.

In addition to the aforementioned challenges, conventional non-viral gene delivery approaches may lead to unwanted immunological responses and oncogenesis, imparted by the presence of bacterial genetic elements in pDNA constructs. These include prokaryotic origins of replication, antibiotic resistance genes, as well as high-frequency immunostimulatory CpG motifs that activate Toll-like receptors in mammalian hosts. In order to improve the immuno-compatibility and durability of pDNA vectors, a new generation of plasmid vector has been constructed that exploit the bacteriophage λ derived integrase (Int)-attP or P1-derived Cre-loxP site-specific recombination systems to generate mini plasmids. These "minicircles" provide safer minimized transgene vectors by removing unwanted prokaryotic elements, thus enhancing bio- and immuno-compatibility in the mammalian host. The smaller size compared to the parental plasmid backbone also confers improved extracellular and intracellular bioavailability leading to efficient gene delivery and hence, improved gene expression.

A second group of modified vectors offering great promise, are linear covalently closed (lcc) plasmid DNA vectors. Aside from the obvious topological differences, lcc double-stranded DNA molecules are torsion-free as they are not subject to gyrase-directed negative supercoiling, and as such possess the properties of linear DNA. However, lcc DNA is not subject to ExoV exonuclease activity in prokaryotes and serum nucleases in mammalian hosts due to covalent linkage of linear ends; preventing degradation of the pDNA vector. Lcc DNA vectors have been constructed by various in vitro strategies including the capping of PCR products. Minimalistic immunogenic defined gene expression (MIDGE) vectors are generated by the digestion of both prokaryotic and eukaryotic backbones after isolation of plasmid from bacterial cells, followed by ligation of the therapeutic expression cassette into hairpin sequences for end-refilling. This technology has shown promising results in various applications including the development of a Leishmania DNA vaccine and a colon carcinoma treatment. MIDGE vectors have also demonstrated up to 17 fold improved transgene expression profile in vivo in some tissues, compared to conventional pDNA vectors. Thus, lcc DNA vectors may in fact outperform their circular counterparts with respect to expression efficiency and bioavailability. However, large-scale production of lcc vectors via existing multistep in vitro processes requires considerable time and financial cost.

E. coli phage N15 was the first discovered temperate phage that does not integrate into its bacterial host genome in its lysogenic (prophage) state and instead exists as a linear covalently closed (lcc)plasmid that is actively partitioned to daughter cells. The ice conformation is conferred by the cleaving joining activity of the protelomerase protein (Prokaryotic Telomerase), TelN (~72 kDa), acting upon the 56 bp telRL target sequence that is entirely sufficient to confer TelN-mediated processing and linearization both in vivo and in vitro. Similarly, phage PY54, isolated from Yersinia enterocolitica, maintains its prophage as a linear, circularly permuted, and covalently closed plasmid with telomere hairpin ends and a genome size of 46 kbp. The paralogous minimal protelomerase target site of PY54 is a 42 bp perfect palindrome, that unlike N15, only partially functions in vivo in the absence of adjacent sequences. The paralogue of the N15 TelN protelomerase, Tel, encodes a 77 kDa protein with observably identical function, able to process recombinant plasmids containing the pal, 42 bp palindromic target site. The tel gene possesses 60% sequence identity to telN and the active recombinases are similar in size (~77 kDa). In addition, there is a partial homology between the 42 bp PY54 pal site and the 56 bp N15 telRL site, where the ten central palindromic nucleotides (5'-TACGCGCGTA-3') (SEQ ID NO: 17) are identical. Despite obvious similarities between the two phages they are evolutionary quite distant, where N15 is more closely related to λ than to PY54. Purified TelN was shown to process circular and supercoiled plasmid DNA containing the identified target site, telRL, to produce linear double-stranded DNA with covalently closed ends. The lcc and mini lcc pDNA vectors produced in vitro by recombinant TelN have been successfully applied in gene delivery experiments, and showed higher and more durable expression of the gene of interest in targeted human cells.

Given the foregoing, it would be desirable to further develop alternative vector systems that provide one or more advantages over existing vectors.

SUMMARY OF THE INVENTION

A novel in vivo vector production system has now been developed that is useful to produce circular or linear covalently closed vectors devoid of bacterial sequences.

Thus, in a first aspect of the invention, a vector production system is provided which comprises recombinant cells designed to encode at least a first recombinase under the control of an inducible promoter, wherein said cells comprise an expression vector adapted to express nucleic acid of interest, wherein said nucleic acid of interest is flanked on either side by a target sequence for at least the first recombinase.

In one embodiment, a vector production system is provided comprising recombinant cells designed to encode at least a first recombinase under the control of an inducible promoter, wherein said cells comprise an expression vector adapted to produce a bacterial sequence-free vector, said expression vector comprising an expression cassette, and a nucleic acid of interest flanked on either side by a target binding sequence for the Tel recombinase and integrated within non-binding regions of the Tel target binding sequence are target binding sequences for one or more additional recombinases.

In another aspect of the invention, a novel expression vector is provided. The vector encodes nucleic acid of interest flanked on either side by a target sequence for at least one recombinase.

In one embodiment, an expression vector adapted to produce a bacterial sequence-free vector is provided, said expression vector comprising an expression cassette, and a nucleic acid of interest flanked on either side by a target binding sequence for the Tel recombinase and integrated within non-binding regions of the Tel target binding sequence are target binding sequences for one or more additional recombinases.

In another aspect, a vector production system comprising recombinant cells designed to encode at least a first recombinase under the control of an inducible promoter, wherein said cells comprise an expression vector adapted to produce a bacterial sequence-free vector, said expression vector comprising backbone sequence, an expression cassette, and a nucleic acid of interest flanked on either side by a target binding sequence for the Tel recombinase and integrated within non-binding regions of the Tel target binding sequence are target binding sequences for one or more additional recombinases, wherein the cells are genetically modified to encode a nuclease genome editing system adapted to cleave the expression vector at a site within the backbone sequence.

In a further aspect of the invention, a method of producing a linear or circular covalently closed vector comprising: incubating a vector production system as above described under conditions suitable to permit expression of the first recombinase; and harvesting the linear or circular covalently closed vector produced by the vector production system.

These and other aspects of the invention will become apparent from the detailed description that follows by reference to the following figures.

DETAILED DESCRIPTION OF THE INVENTION

Figure 1:
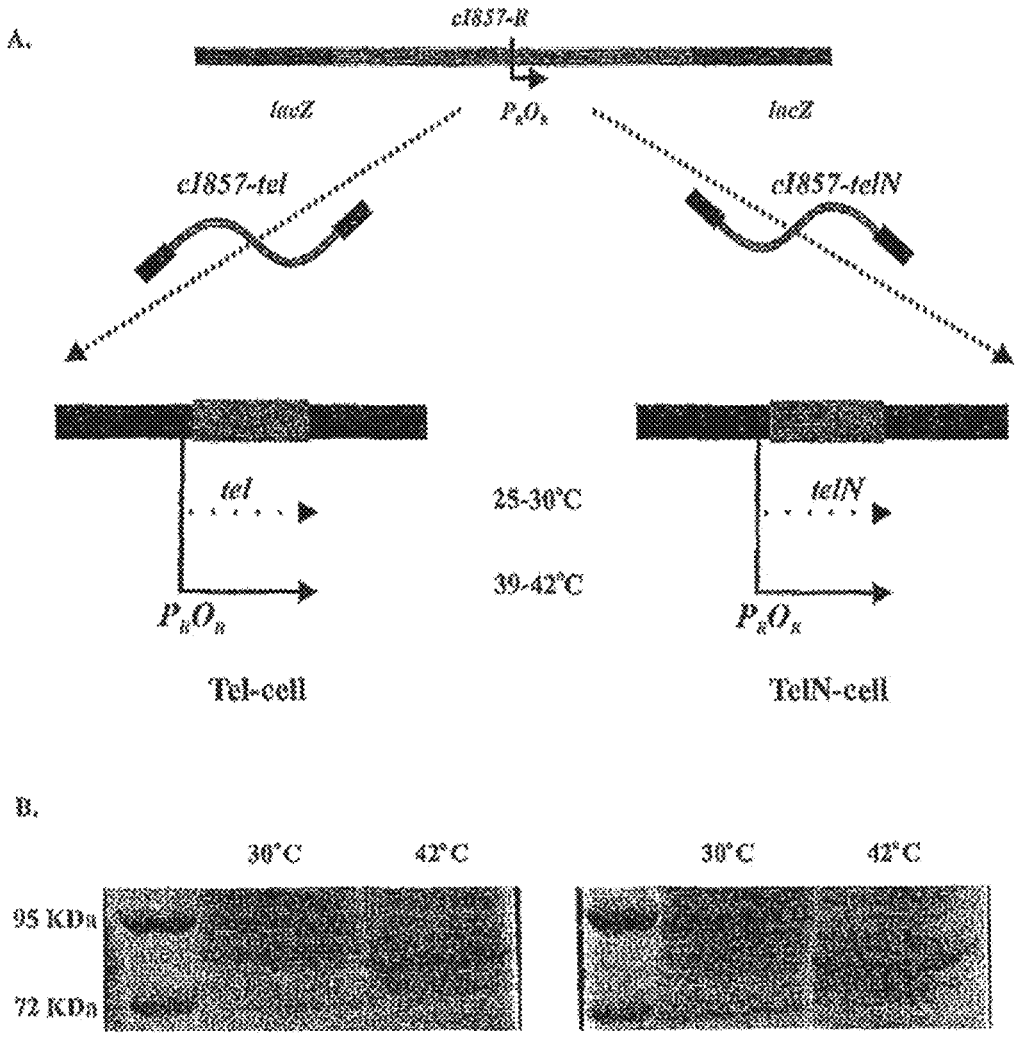
FIG. 1. R-cell construction and temperature-regulated expression of Tel and TelN. A. R-cell construction and temperature-regulated expression of recombinases, Tel and TelN. The cI857-R cassette was inserted into the lacZ gene of E. coli by homologous recombination. Under repressed (25-30° C.) conditions, the λ temperature-sensitive CI857 repressor binds to λ operators to inhibit transcription of the recombinase gene, but upon shifting to 40-42° C., the repressor is labile, falling off operators and induces expression of the recombinase from the strong λ $P_L$ promoter. B. Controllable Tel and TelN expression from R-cells. Expression of the recombinase proteins Tel and TelN under repressed (30° C.) and induced (42° C.) conditions from total R-cell extract. Lane 1: Weight marker; Lane 2: Recombinase.

A vector production system for use to produce mini linear or circular covalently closed nucleic acid vectors is provided which comprises recombinant host cells designed to express a first recombinase under the control of an inducible promoter, wherein said cells comprise an expression vector adapted to express nucleic acid of interest which is flanked on either side by a target sequence for at least the first recombinase.

The system comprises recombinant host cells. Suitable host cells for use in the present production system include microbial cells, for example, bacterial cells such as E. coli cells, and yeast cells such as S. cerevisiae. Mammalian host cells may also be used including Chinese hamster ovary (CHO) cell for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651; murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

The host cell is designed to encode at least one recombinase. The host cell may also be designed to encode two or multiple recombinases. The term "recombinase" refers to an enzyme that catalyzes DNA exchange at a specific target site, for example, a palindromic sequence, by excision/insertion, inversion, translocation and exchange. Examples of suitable recombinases for use in the present system include, but are not limited to, TelN, Tel, Tel (gp26 K02 phage) Cre, Flp, phiC31, Int and other lambdoid phage integrases, e.g. phi 80, HK022 and HP1 recombinases. The target palindromic sequences for each of these recombinases are, respectively:

```
the telRL site
                                        (SEQ ID NO 1)
(TATCAGCACACAATTGCCCATTATACGCGCGTATAATGGACTAT

TGTGTGCTGA);


the pal site
                                        (SEQ ID NO: 2)
(ACCTATTTCAGCATACTACGCGCGTAGTATGCTGAAATAGGT);


          the φK02 telRL site
                                        (SEQ ID NO: 3)
          (CCATTATACGCGCGTATAATGG);


     the loxP site
                                        (SEQ ID NO: 4)
     (TAACTTCGTATAGCATACATTATACGAAGTTAT);


   the FRT site
                                        (SEQ ID NO: 5)
   (GAAGTTCCTATTCTCTAGAAAGTATAGGAACTTC);


the phiC31 attP site
                                        (SEQ ID NO: 6)
(CCCAGGTCAGAAGCGGTTTTCGGGAGTAGTGCCCCAACTGGGGT

AACCTTTGAGTTCTCTCAGTTGGGGGCGTAGGGTCGCCGACAYGA

CACAAGGGGTT);


the λ attP site
                                        (SEQ ID NO: 7)
(TGATAGTGACCTGTTCGTTTGCAACACATTGATGAGCAATGCTT

TTTTATAATGCCAACTTTGTACAAAAAAGCTGAACGAGAAACGTA

AAATGATATAAA).
```

Recombinant host cells encoding at least one recombinase are prepared using techniques well-established in the art. For example, nucleic acid encoding a selected recombinase is introduced into the cell using a suitable vector under conditions appropriate for cell transformation. The recombinant host cells may be transformed via an expression vector, or by integration of recombinase-encoding nucleic acid into the host cell genome.

Expression of the recombinase is under the control of any regulated or inducible promoter, i.e. a promoter which is activated under a particular physical or chemical condition or stimulus. Examples of suitable promoters include thermally-regulated promoters such as the λ pL promoter, the IPTG regulated lac promoter, the glucose regulated ara promoter, the T7 polymerase regulated promoter, cold-shock inducible cspA promoter, pH inducible promoters, or combinations thereof, such as tac (T7 and lac) dual regulated promoter.

The recombinant cells also incorporate an expression vector adapted to express a nucleic acid of interest. The expression vector includes regulatory expression sequences, e.g. promoter, initiation and termination sequences, and a nucleic acid sequence of interest appropriately positioned relative to the regulatory sequences so that expression of the nucleic acid of interest will occur, i.e. the nucleic acid of interest is expressibly incorporated within the expression vector. The regulatory expression sequences and nucleic acid sequence of interest, i.e. the expression cassette, is flanked on either side by a target sequence (e.g. target nucleic acid sequence) for at least a first recombinase.

The expression vector may also include target sequence on either side of the nucleic acid sequence of interest for additional recombinases to increase the versatility of the system and render it useful with a range of recombinases to produce either circular or linear covalently closed vectors. These additional target sequences may or may not be integrated within the target sequence for the first recombinase. To produce a more compact expression vector, additional recombinase target sequences are integrated within the first recombinase target site. Thus, the expression vector may include a target sequence for the first recombinase flanking the nucleic acid of interest, and integrated within each target sequence for the first recombinase sequence, at regions which do not have an impact on recombinase activity, e.g. inactive, non-binding regions, may be target sequences for one or more additional recombinases. For example, the expression vector may include the pal site as the target site for the first recombinase, flanking the nucleic acid of interest, and integrated within each of the pal sites, at inactive regions within the pal sites, may be target sites for one or more additional recombinases such as the telRL site, the loxP site, the FRT site, the attP site and combinations/variations of these target sites for the purposes of recombination-mediated cassette exchange (RMCE). In one embodiment, the expression vector incorporates multiple additional recombinase target sites within the first recombinase target site. For example, the expression vector includes a pal target sequence flanking the nucleic acid of interest, and integrated within the non-binding regions of the pal sequence so as not to disrupt Tel/pal activity of pal are telRL, loxP, FRT, and attP. Thus, the size of the multi-target site is minimized by the integration of five different recombinase target sites within 300 bp while maintaining multi-target functionality.

As one of skill in the art will appreciate, the expression vector encoding a nucleic acid sequence of interest may additionally include sequence, upstream or downstream of the recombinase target sequences, that functions to facilitate the function of the production system. For example, the vector may incorporate an enhancer sequence that facilitates or enhances nuclear translocation or transfection of the resultant vector. Enhancers can include any transcriptional enhancer binding sequence such as viral enhancer sequences, e.g. Simian Virus (SV) 40 or Hepatitis B Virus (HBV) enhancers, or tissue specific enhancer sequences such as any transcriptional factor binding sequence that is specifically expressed in that tissue, e.g. GADD45G target sequence in human cortex, ventral forebrain and thalamus.

As one of skill in the art will appreciate, the expression vector may incorporate any nucleic acid of interest to be expressed or delivered by the mini vector product. The nucleic acid of interest, thus, may be DNA or RNA. The nucleic acid of interest may be selected for the therapeutic utility of the protein product it encodes, for example, a protein product for use in the treatment of a disease condition such as ornithine transcarbamylase deficiency (OTCD), for example, the nucleic acid of interest to treat this condition would encode the corrected form of ornithine transcarbamylase enzyme. The mini vector product may also be used to deliver a DNA vaccine such as an HIV Env-Gag VLP sequence; a molecular adjuvant such as 11-12; or nucleic acid encoding a prodrug activating enzyme such as thymidine kinase in the treatment of various cancers.

The present mini vector product may incorporate nucleic acid useful for gene editing, for example, a nuclease genome editing system. Examples of nuclease genome editing systems include, but are not limited to, Clustered Regularly Interspaced Short Palindromic Repeats (CRISPR) nuclease system, e.g. including a targeting gRNA and a CRISPR-associated (Cas) gene, such as CRISPR-Cas9, Transcription Activator-Like Effector Nucleases (TALEN) and mito-TALEN, ZFN Zinc-Finger Nucleases (ZFN).

In one embodiment, the present mini vector product incorporates nucleic acid encoding a CRISPR nuclease system, such as a CRISPR/Cas9 Type II genome editing system, including a Cas nuclease, and a guide RNA (gRNA), The Cas nuclease may, for example, be a Cas 9-based nuclease. Examples of Cas 9 nucleases include wild-type Cas 9 (a double nickase) from Streptococcus pyogenes (SP), Staphylococcus aureus (SA), Neisseria meningitidis (NM), Streptococcus thermophilus (ST), and Treponema denticola (TD), as well as mutated recombinant Cas 9, e.g. mutated to function as a single nickase such as Cas9 D10A and Cas9 H840A. The mutated Cas 9 may also be a nuclease-deficient Cas (for example, incorporating both D10A and H840A to inactivate nuclease function) which binds but does not cleave and thereby silences a gene. Nuclease-deficient Cas 9 may be used to prevent or minimize expression of a dysfunctional mutated protein, which may interfere with the activity of the desired functional protein.

The gRNA comprises a fusion of a targeting RNA sequence, crRNA (CRISPR RNA) and a trans-activating RNA (tracrRNA). The crRNA and tracrRNA are selected based on the selected Cas nuclease. The targeting sequence of the guide RNA (gRNA) is a strand of RNA that is homologous to a region on a target gene, i.e. a gene to be edited or silenced. Target genes may be genes associated with genetic disease such as cystic fibrosis, muscular dystrophy, lysosomal storage disease, and others. The targeting RNA may comprise from 10-30 nucleotides, e.g. from 15-25 nucleotides, and may comprise a GC content of about 40-80%. The CRISPR system may be utilized to disrupt expression of a gene by insertion or deletion of nucleotides to the target gene. The CRISPR system may also be used to edit (e.g. to correct a gene mutation) by homology directed repair in which the targeting RNA includes an editing region, e.g. a region that incorporates an edit to be incorporated into the target gene, flanked by a region of homology (homologous arms) on either side thereof which range in size from about 100-800 nucleotides or more, depending on the size of the editing region. The size of the editing region is not particularly restricted, and may include a single nucleotide edit, or edits of up to 100 nucleotides or more. The targeting sequence of the gRNA is selected such that it targets a site within the target gene that is proximal (e.g. within about 2-5 nucleotides or more) to a protospacer adjacent motif (PAM) located within the target gene. The PAM is recognized by the Cas nuclease and permits Cas nuclease binding. The gRNA additionally incorporates related crRNA and a tracrRNA sequences, which interact and function to direct the Cas nuclease to the target gene and catalyze cleavage of the target gene by the Cas nuclease. As will be understood by one of skill in the art, while each of the crRNA, tracrRNA, and Cas nuclease sequences are related, these sequences may be native or mutated sequences, provided that any mutations thereof do not have an adverse impact on function. Methods for selection of suitable crRNA and tracrRNA sequences for use in gRNA are known in the art.

The targeting RNA is an RNA strand complementary to a site on the target gene which is 3-4 nucleotides upstream of a PAM sequence recognized by the Cas nuclease. The targeting RNA does not itself include a PAM sequence. PAM sequences differ for various Cas nucleases. For example, for Streptococcus pyogenes (SP), the PAM sequence is NGG; for S. aureus, the PAM sequence is NNGRRT or NNGRR (N); for Neisseria meningitides, the PAM sequence is NNNNGATT; for Streptococcus thermophilus, the PAM sequence is NNAGAAW; for Treponema denticola (TD), the PAM sequence is NAAAAC. "N" represents any nucleotide, W=weak (A or T) and R=A or G.

Nucleic acid encoding a nuclease genome editing system, such as a selected CRISPR nuclease system including gRNA and a Cas nuclease, may be produced using known synthetic techniques for incorporation into an expression vector and flanked by one or more recombinase target sites in accordance with the invention.

In another embodiment, the host cells may be genetically modified to encode a nuclease genome editing system to assist with purification following mini vector production, e.g. to eliminate any unprocessed parental precursor plasmid as well as any linear DNA by-product resulting from the generation of mini vectors in the cell. Examples of nuclease genome editing systems include, but are not limited to, Clustered Regularly Interspaced Short Palindromic Repeats (CRISPR) nuclease system, e.g. including a targeting gRNA and a CRISPR-associated (Cas) gene, such as CRISPR-Cas9, Transcription Activator-Like Effector Nucleases (TALEN), and ZFN Zinc-Finger Nucleases (ZFN).

In one embodiment, the host cell is modified to incorporate nucleic acid encoding a CRISPR nuclease system, such as a CRISPR/Cas9 Type II genome editing system, including nucleic acid encoding a Cas nuclease, and guide RNA (gRNA) that targets corresponding sequence within backbone sequence of the expression vector encoding the gene of interest. The Cas nuclease may, for example, be a Cas 9-based nuclease. Examples of Cas 9 nucleases include wild-type Cas 9 (a double nickase) from Streptococcus pyogenes (SP), Staphylococcus aureus (SA), Neisseria meningitidis (NM), Streptococcus thermophilus (Sr), and Treponenma denticola (TD).

In this case, the CRISPR system is utilized to target and cleave sequence embedded in the expression vector backbone (i.e. backbone sequence is sequence innate to the expression vector and outside of the recombinase target binding sequences) once the mini-vector containing the gene of interest is produced. Cleavage of the vector backbone subjects this nucleic acid to exonuclease degradation. The CRISPR system is under the control of an inducible promoter, and following mini-vector production, is induced. Upon induction, the Cas 9 nuclease and gRNA are expressed, the gRNA guides the Cas9 nuclease to the vector backbone. Cas 9 cleaves the backbone as well as any unprocessed parent plasmid, subjecting both to nuclease degradation. This results in purification of the reaction mixture, as the only product remaining is DNA mini-vector product which does not incorporate the target site for Cas9-gRNA.

A recombinant host cell in accordance with the present invention, encoding at least a first recombinase and including an expression vector encoding an expression cassette including a nucleic acid sequence of interest flanked by at least the target site for the first recombinase will generate mini linear covalently closed or mini circular covalently closed vectors, depending on the nature of the recombinase.

Thus, a method for producing a linear or circular covalently closed vector is also provided. The method comprises the step of incubating the vector production system under conditions suitable to permit expression of at least a first recombinase, and optionally two or more recombinases, by the system. The expressed recombinase recognizes its target sequence within the expression vector and catalyzes site specific recombination at the target sequence to yield a linear or circular covalently closed vector including the nucleic acid of interest within its expression cassette. The present method, thus, advantageously provides an efficient single step process for producing linear and circular covalently closed vectors that incorporate a nucleic acid of interest.

The mini linear or circular covalently closed vector product of the present in vivo production system will vary with the recombinase/target sequence encoded. To produce a linear covalently closed vector, a system engineered to encode the recombinase, TelN or Tel, and incorporating an expression vector encoding the appropriate target sequence is utilized. To produce a circular covalently closed vector, a system engineered to encode a recombinase such as Cre or Flp, and which incorporates a vector encoding the appropriate target sequence is utilized.

The present bacterial sequence-free mini linear and circular covalently closed vectors provide superior alternatives to traditional plasmids. Bacterial sequence-free mini vectors exhibit better bioavailability compared to conventional pDNA vectors due to their smaller size, and improved immuno-compatibility which is due to the reduction or elimination of unwanted prokaryotic sequence. In addition, their smaller size confers higher transfection efficiency and higher copy numbers of the vector per unit mass, resulting in lower toxicity due to the need for less transfection reagent.

Although the mini vectors may be used in naked form, they may also be modified to enhance their utility. For example, the mini vector product may be utilized with a transfection reagent, e.g. a cationic liposome reagent such as Lipofectamine™ or a cationic polymer reagent such as JetPRIME™, carbon nanotubes, or gold particles to form lipoplexed or polyplexed covalently closed vectors, respectively, which have enhanced transfection efficiency.

The mini vectors themselves are useful to express a protein of interest encoded by a nucleic acid of interest by the mini vector. Thus, a method of producing a protein is also provided herein using a mini vector in accordance with an aspect of the invention. The method comprises the steps of: producing a mini linear or circular covalently closed vector using the present vector production system, wherein the protein is encoded by the nucleic acid sequence of interest incorporated within the mini vector; transfecting a cell with the mini vector and incubating the cell under conditions suitable to permit expression of the protein.

Embodiments of the invention are described in the following example which is not to be construed as limiting.

Example 1

Methods

Strains and Plasmids

E. coli K-12 strains were used in the generation of all recombinant cell constructs and DH5α and JM109, in particular, were employed as hosts for plasmid constructions and amplification.

A list of bacterial and phage strains used in this study are shown in Table 1.

TABLE 1

Bacteria, Phage and Plasmids.

| Strain | Genotype [1] | Source |
|---|---|---|
| | Bacteria | |
| BW23474 | F-, Δ(argF-lac)169, ΔuidA4::pir-116, recA1, rpoS396(Am)?, endA9(del-ins)::FRT, rph-1, hsdR514, rob-1, creC510 | E. coli Genetic Stock Center (CGSC) # 7838 [39] |
| DH5α | F-, Δ(argF-lac)169, φ80dlacZ58(M15), ΔphoA8, glnV44(AS), λ⁻, deoR481, rfbC1?, gyrA96(NalR), recA1, endA1, thi-1, hsdR17 | CGSC # 12384 |
| DH5α λpir | F-, Δ(argF-lac)169, endA1, pir⁺, recA1 | Gift from Dr. T. Charles; [40] |
| JM109 | F', Δ(gpt-lac)0, glnV44(AS), λ⁻, rfbC1?, gyrA96(NalR), recA1, endA1, spoT1?, thi-1, hsdR17, pWM5, F128-x | New England Biolabs |
| W3101 | F-, λ⁻, galT22, IN(rrnD-rrnE)1, rph-1 | CGSC # 4467; |
| W3110 | F-, λ⁻, IN(rrnD-rrnE)1, rph-1 | CGSC # 4474; [41] |
| W3110-Cre (W1NN) | F-, λ⁻, IN(rrnD-rrnE)1, rph-1 lacZ::Cm-cI857-cre | This study |
| W3110-TelN (W2NN) | F-, λ⁻, IN(rrnD-rrnE)1, rph-1 lacZ::Cm-cI857-telN | This study |
| W3110-Tel (W3NN) | F-, λ⁻, IN(rrnD-rrnE)1, rph-1 lacZ::Cm-cI857-tel | This study |
| | Phages | |
| N15 | Wild type (wt) (telN⁺, tos⁺) | Gift from Dr. S. Hertwig; [21] |
| P1 | wt (cre⁺, loxP⁺) | Gift from Dr. B. Funnell; [42] |
| PY54 | wt (tel⁺, pal⁺) | Gift from Dr. S. Hertwig; [21] |
| | Plasmids | |
| pAH120 | attP λ integration plasmid ($Kn^R$) | NBRP [25] |
| pAH123 | cI857-pL-int Φ80 ($Ap^R$) | NBRP [25] |
| pAH153 | attP Φ80 integration plasmid ($Kn^R$) | NBRP [25] |
| pBRINT | lacZ::cat-MCS::lacZ ($Cm^R$) | NBRP; [37] |
| pGL2 | SV40P-Luc-PolyA-SV40 intron | Promega |
| pInt | cI857-pL-int λ ($Ap^R$) | NBRP [25] |
| pNN1 | cI857-pR-pL-cre-tL ($Ap^R$) | This study |
| pNN2 | cI857-pR-pL-tel-tL ($Ap^R$) | This study |
| pNN3 | cI857-pR-pL-telN-tL ($Ap^R$) | This study |
| pNN4 | lacZ::cat- cI857-pR-pL-cre-tL::lacZ ($Cm^R$) | This study |
| pNN5 | lacZ::cat- cI857-pR-pL-tel-tL::lacZ ($Cm^R$) | This study |
| pNN6 | lacZ::cat- cI857-pR-pL-telN-tL::lacZ ($Cm^R$) | This study |
| pNN7 | pGL2-egfp switched for luc | This study |
| pNN8 | pNN7 + SS (upstream of SV40 promoter) | This study |
| pNN9 | pNN8-SS (2XSS) (second SS downstream of SV40 polyA sequence) | This study |
| pNN10 | pAH120 (SS⁺) | This study |
| pNN11 | pAH153 (SS⁺) | This study |
| pPL451 | cI857-pR-pL-MCS-tL ($Ap^R$) | Accession # AB248919 National Bioresource Project (NBRP); [43] |

[1] sequences of interest confirmed by PCR and/or sequencing

Construction of Recombinant Cells (R-Cells)

W3110 ($recA^+$) E. coli was used for chromosomal engineering studies and in vivo recombinase-expression as follows. Protelomerase coding gene tel was amplified from bacteriophage PY54 lysate using the following primers: Tel-F 5'-GCGGATCCTGGGTTAATTTGTGTGTT-3' (SEQ ID NO: 8) and Tel-R 5'-CG CTCGAGTTACTCCATATTTTCAGTCCATGCTTGT-3' (SEQ ID NO: 9) (annealing Tm 64° C.). Protelomerase coding gene telN was amplified from bacteriophage N15 lysate using primers: TelN-F 5'-ATC GGATCCCGATATCCAGAGACTTAGAAACGGG-3' (SEQ ID NO: 10) and TelN-R 5'-ATATA AAGCTTCTTTTAGCTGTAGTACGTTTCCCATGCG-3' (SEQ ID NO: 11) (annealing Tm 62° C.). As a positive control for in vivo production of modified pDNA vectors, the recombinase encoding gene cre was amplified from bacteriophage Plrev6 lysate using primers: Cre-F 5'-GG AATCCGGTCGCTGGCGTTTCTATGAC-3' (SEQ ID NO: 12) and Cre-R 5'-CG CTCGAGTGAATATTAGTGCTTACAGACAG-3' (SEQ ID NO: 13) (annealing Tm 66° C.). Italicized regions denote restriction sites for BamHI, XhoI, HindIII, and EcoRI. PCR amplifications were conducted using Phusion Flash High-Fidelity PCR Master Mix (New England Biolab) for 30 s at 98° C. for initial denaturation, 30 cycles of 5 s at 98° C., 10 s at annealing Tm, 45 s at 72° C., and 2 min at 72° C. for final extension to generate cre (1.3 kb), tel (2.1 kb), and telN (2.3 kb) fragments. Constructs were tested and confirmed by colony PCR and analytical digestion. PCR products were purified from 0.8% agarose gel (Qiagen Gel extraction kit), and digested with the listed enzymes (New England Biolabs). Recombinase genes were cloned into the MCS of the inducible prokaryotic expression vector pPL451

(Accession #AB248919) to produce pNN1, pNN2, and pNN3 vectors. pPL451 (4.2 kb) imparts temperature-regulated expression of the cloned gene via CI[Ts]857-mediated repression of the λ $P_L$ strong promoter. A list of plasmids used or constructed in this study is shown in Table 1. All primers were designed using the Gene Runner 3.01 (Hastings Software, Inc) and synthesized commercially (Sigma-Aldrich, Inc). R-cells were constructed via insertion of recombinase genes into E. coli W3110 chromosome using the pBRINT-Cm integrating plasmids, which facilitate the homologous recombination and chromosomal integration of cloned sequence of interest into the lacZ gene of E. coli. For each plasmid construct encoding inducible expression of a cloned recombinase in pPL451, the cI857-$P_L$-X-$t_L$ cassette (where X=cre, tel or telN) was amplified from the pNN1 to 3 constructs by the cI857X-F 5'-TCC CCGCGGAGCTATGACCATGATTACGAATTGC-3' (SEQ ID NO: 14), cI857telN/cre-R 5'-GG ACTAGTCCCCATTCAGGCTGCGCAACTGTTG-3' (SEQ ID NO: 15), and cI857tel-R 5'-GC TCTAGAGCAGGCTGCGCAACTGTTGGGAAG-3' (SEQ ID NO: 16) primers with SacII, SpeI, and XbaI sites respectively. The amplified cassettes were cloned into the MCS of pBRINT ($Cm^R$) plasmid to produce pNN4, pNN5, and pNN6 integrating vector constructs. Amplification was performed by the Phusion Flash High-Fidelity PCR Master Mix (New England Biolab) for 10 s at 98° C. for initial denaturation, 30 cycles of is at 98° C., 5 s at 68° C., 120 s at 72° C., and 1 min at 72° C. for final extension to generate cI857-cre (2.8 kb), cI857-tel (3.2 kb), and cI857-telN (3.5 kb) fragments. Constructs were tested and confirmed by colony PCR and analytical digestion.

E. coli cells were grown in Luria-Bertani (LB) medium and plated on LB-Agar plates composed of 1.0% Tryptone, 0.5% Yeast Extract, 1.0% NaCl, pH 7.0. Antibiotics (Ab) (Sigma-Aldrich, Inc). were used at the following concentrations for the growth of cells carrying multicopy plasmids: Ampicillin (Ap, 100 ug/ml in H2O), Chloramphenicol (Cm, 25 ug/ml in isopropanol), Gentamycin (Gm, 15 ug/ml in H2O), and Kanamycin (Km, 50 ug/ml in H2O) H2O used for dilution of primers, plasmids, antibiotics, and production of competent cells is nuclease-free sterile molecular grade water (Sigma-Aldrich, Inc). To achieve chromosomal integration of the pNN4 to 6 constructs into $Rec^+$ W3110, a 1:100 dilution of fresh overnight cells was grown on SOB media at 37° C. to $A_{600}$=0.4-0.6 and cells were harvested by centrifugation at 5K RPM for 5 min. Cells were washed in water three times and W3110 cells were transformed by 1 ug of pNN4, 5, or 6 integrating vectors via electroporation at 800 v. Cells were recovered in SOC at 30° C. for 1 h, then spread onto selective media on chloramphenicol (Cm, 12.5 ug/ml), 100 ug/ml of 5-bromo-4-chloro-indolyl-β-D-galactopyranoside (X-Gal) (Promega) and 0.1 mM Isopropyl β-D-1-thiogalactopyranoside (IPTG) (Sigma-Aldrich, Inc) added LB agar plates and incubated overnight at 30° C. To make a 50 mg/ml stock solution, 500 mg X-Gal was dissolved in 10 ml dimethylformamide. The plates were protected from light. White colonies were selected and further screened for sensitivity to ampicillin (Ap) and Cm. White, $Ap^S$ colonies indicated loss of the pNN integrating plasmids after disruptive insertion of the cI857-$P_L$-X-$t_L$ cassette into the lacZ gene, generating recombinant derivatives, W1NN, W2NN, and W3NN (Freezer #158-159-160) (Table 1). W3110 [lacZ::Cm-cI857(cre/tel/telN)] recombinants were confirmed for presence of the cI857-$P_L$-X-$t_L$ cassette and temperature-regulated, conditional expression of recombinanse, by colony PCR using Taq polymerase enzyme (NEB), sequencing (Sigma), and SDS PAGE (Bio-Rad) at various temperatures between 30° and 42° C. For the selection of cells carrying the Ab markers integrated in the chromosome, the following concentrations were used: Cm (12.5 ug/ml), Gm (5 ug/ml), and Km (20 ug/ml).

Construction of Modified/New Generation of pDNA Vectors

The multi-purpose recombinase target site, named Supersequence (SS), was designed to carry Cre, Flp and TelN minimal targets sites (loxP-FRT-telRL) respectively, all within the Tel 142 bp pal sequence, which provides the PY54 derived Tel target site. SS also carries a 78 bp SV40 enhancer sequence that flanks each side of the pal sequence to facilitate nuclear translocation and enhancing transfection efficiency. The SS fragment was synthesized by the GeneScript and cloned into the pUC57 by EcoRI and HindIII. Commercial expression vector, pGL2-promoter (5.8 kb) (Promega), was modified by replacement of the luc gene (1.65 kb) with egfp (790 bp) from pGFP (clontech) to form pNN7 (Genescript, Inc.) (4.9 kb) Next, SS was cloned immediately upstream of the SV40 promoter+intron site of pNN7 to form pNN8 (5.3 kb). Then the SS fragment was cloned downstream of the poly A site of pNN8 to form pNN9 (5.6 kb). This plasmid carries 2 SS sites that flank the EGFP gene cassette. The multicopy plasmid can be conformed to mini circular (ccc) vector (mediated by Cre-loxP; Flp/FRT), or mini linear covalently closed (lcc) vector (mediated by TelN-telRL; Tel/pal). R-cells were transformed by 1 ug of pNN7 to 9 DNA constructs on LB+Ap (50 ug/ml) to $A_{600}$=0.6 at 30° C. with aeration. To induce recombinase expression and plasmid conformational conversion, transformed R-cells were heat shocked to induce the recombinase expression at 42° C. for 30 min at mid-logarithmic phase of bacterial growth, before being transferred to 30° C. overnight. Cells were then harvested and plasmid extracted (Omega mini plasmid extraction kit, VWR). Plasmid topology was assayed by agarose gel electrophoresis and digestion. Standard recombinant DNA techniques were performed as described by Sambrook et al. (1989).

Chromosomal Integration Assays of Linear Covalently Closed (LCC) DNA

CRIM (conditional-replication, integration, and modular) plasmids (as described in Haldimann et al. 10.1128/JB.183.21.6384-6393.2001. J Bacteriol 2001, 183(21): 6384-6393) that possess a R6K origin of replication and a phage attachment (attP) site were modified to carry the SS fragment. SS was cloned into the pAH120 and pAH153 constructs (from NBRP; Table 1) by ClaI and BamHI (NEB) to generate the pNN10 (3.3 kb) and pNN11 (2.6 kb) constructs, respectively. Plasmids were integrated into the host bacterial attachment (attB) site by supplying phage integrase (Int) from the helper plasmids. Plasmid pNN10 and pNN11 constructs were amplified in DH5α(λpir) or BW23474, and the successful clones were confirmed by restriction pattern digestion and colony PCR. Int helper plasmids pINT-ts (int λ) and pAH123 (Int Φ180) that express int from λ$P_L$ under cI857 control and carry a temperature sensitive pSC101 ori were used for integration of CRIM, pNN10 and pNN11 plasmids into their corresponding chromosomal attB sites of pir hosts that are non-permissive for plasmid replication.

R-Cells W1NN, W2NN, and W3NN (Freezer #158-159-160) (Table 1) W3110 [lacZ::Cm-cI857(cre/tel/telN)] were grown in 2 ml of SOB cultures at 30° C. to an optical density of $A_{600}$=0.6 and then electroporated and transformed by 50 ng helper plasmids pINT-Ts (int λ) or pAH123 (int Φ80) and selected on LB+Ap agar at 30° C. R-Cells carrying helper plasmids were grown in 50 ml of SOB+Amp at 30° C. to $A_{600}$=0.6 then transformed by 1 ug of pAH120, pNN10

(pAH120+SS), pAH153, pNN11 (pAH153+SS) DNA, suspended in SOC at 37° C. for 1 h for recovery and Int expression and at 42° C. for 30 min for loss of helper plasmid, then selected on LB+Ab (Km, 15 ug/ml for pAH120, pNN10 and Gm, 5 ug/ml in case of pAH153, pNN11) and incubated overnight at 37° C. Stable integrated colonies and loss of the helper plasmid were selected by growing cells on selective media (Ap, 50 ug/ml). Single-copy integrants W4NN to W15NN, (pAH120, pNN10 (pAH120+SS), pAH153, pNN11 (pAH153+SS) DNA integrated into the W3110 [lacZ::Cm-cI857(cre/tel/telN)]) were screened and selected by PCR using predesigned primers, (as described in Haldimann et al).

Viability Assays of Linear Covalently Closed (LCC) DNA Integration

Single copy pAH120, pNN10 (pAH120+SS), pAH153, pNN11 (pAH153+SS) DNA integrants W4NN to W15NN (Freezer #200 to 212) were isolated on selective media (15 ug/ml Km for pAH120, pNN10 and 5 ug/ml Gm in case of pAH153, pNN11).

Integrants were grown in 2 ml of LB cultures at 30° C. to an optical density of $A_{600}$=0.4 and divided into two 1 ml cultures for repressed Cre/Tel/TelN expression at 30° C. and induced Cre/Tel/TelN expression at 42° C. to an optical density of $A_{600}$=1.00.

Cells were spread in selective media and grown overnight at 30° C. and 42° C. Viability was assayed by colony counting and size of the colonies grown at 30° C. versus 42° C.

Visualization of Cells

Cells were visualized by gram staining. Briefly, integrated cells were grown in 2 ml of LB+selective antibiotic from freshly grown cells at 30° C. to early log phase $A_{600}$=0.2 and then were divided in two tubes and grown at 30° C. and 42° C. for 1 h to late log phase, $A_{600}$=0.8. Bacterial smears were then prepared on the slide, heat fixed and gram stained. Pictures of bacteria were taken at 100× magnification. From pictures, 400 random cells were chosen for measurement under all tested conditions.

Results

R-Cells Exhibit Temperature-Regulated Recombinase Expression

Recombinant cells were constructed that place tel or telN recombinase genes under control of the bacteriophage λ strong promoter, pL, that is regulated by the temperature-sensitive λ repressor, CI[Ts]857 (FIG. 1). Positive cre-expressing control cells were similarly prepared. Total cellular protein in tel and telN R-cells under repressed and fully induced (42° C.) conditions was examined. As expected, both R-cells demonstrated minimal recombinase protein levels, identified at 72 KDa for both TelN and Tel at 30° C., where CI[Ts] actively binds the $O_L$ operator and represses transcription of the downstream recombinase gene. Upon shifting cells to 42° C., where repressor activity is completely abrogated and occlusion of pL promoter activity is relieved, prominent recombinase expression was observed. These results confirm that the constructed Tel- and Tel-N cells are temperature inducible for recombinase production.

Figure 2:
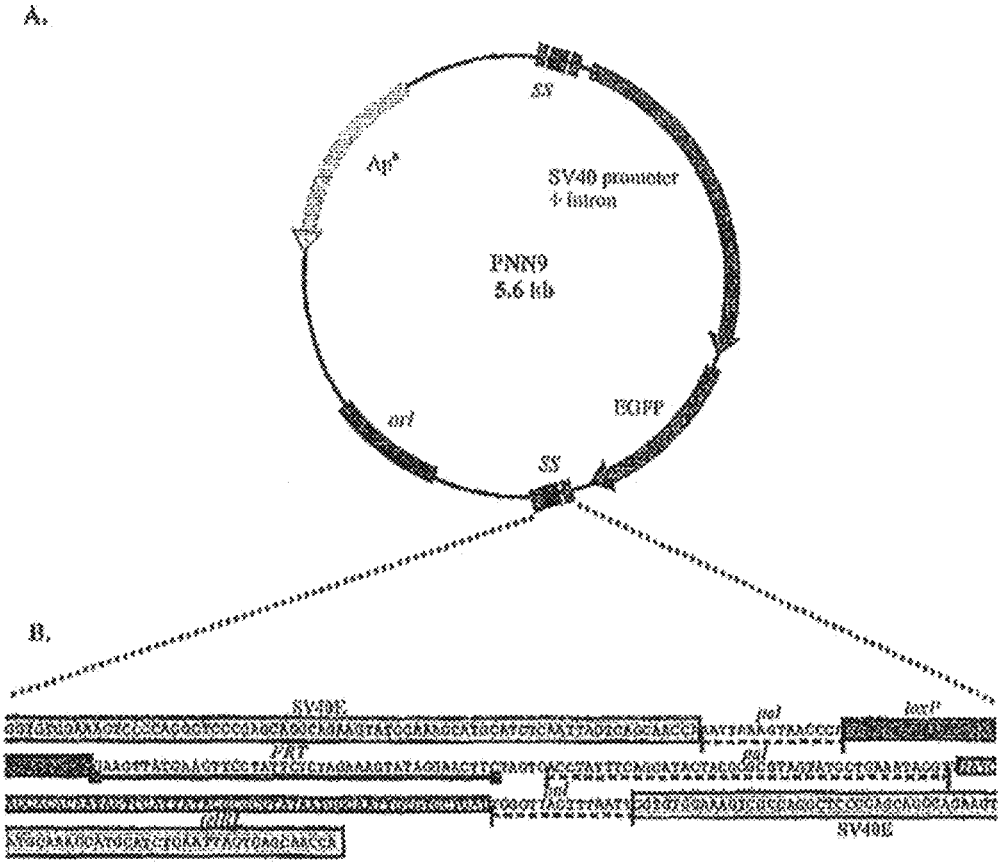
FIG. 2. Parent plasmid pNN9 and "Super Sequence" multi target site. A. Map of the parent pNN9 construct. The map denotes location of primary genetic elements, including the designed and integrated Super Sequence (SS). B. Map of the Super Sequence construct. The map includes relative locations of SV40 enhancer sequences as well as the telRL, loxP and FRT sequences integrated into non-binding regions of the 142 bp pal (Tel) target site.
Figure 3:
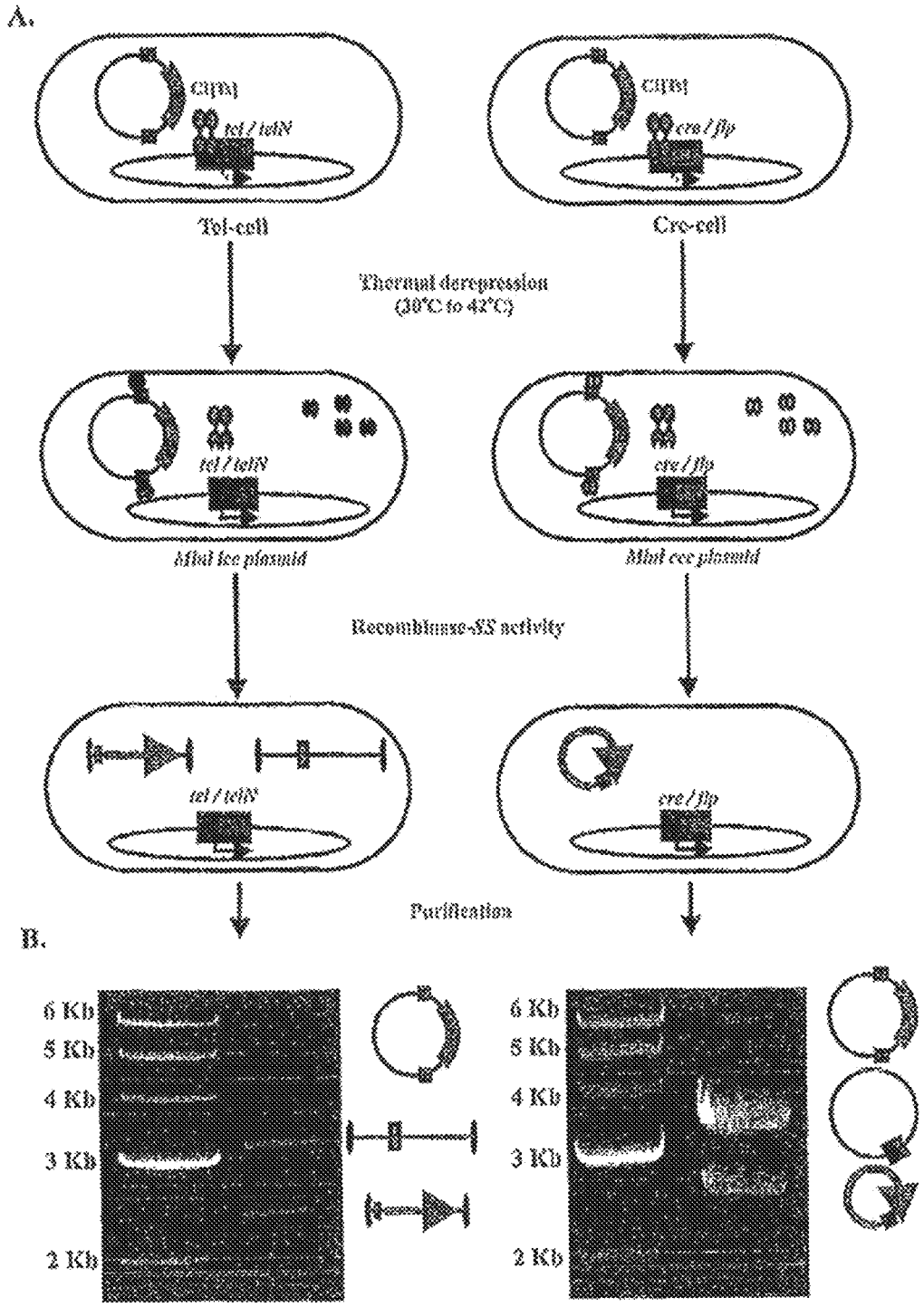
FIG. 3. Conditional processing of the parent plasmid DNA vectors. A. R-cell conditional processing of the parent pNN9 plasmid into mini DNA vectors. Under induced conditions, R-cells lead to the production of mini lcc (Tel-cell) and mini ccc (Cre-cell) DNA. B. Processing of the parent plasmid construct into mini lcc and mini cc vectors. Efficiency of processing of the pNN9 plasmid into lcc mini vectors (Tel) and ccc mini vectors (Cre) after plasmid extraction from R-cells under induced (42° C.) conditions. Schematics adjacent to each band show the plasmid and expected conformation.

In combination with the R-cell system, a eukaryotic egfp-expression vector that carries two specialized 343 bp sequences placed upstream of the SV40 promoter and downstream of the polyadenylation signal of the minimal egfp expression cassette (pNN9; FIG. 2A) was constructed. This construct, termed "Super Sequence" (SS) carries a modified pal target sequence of Tel, with integrated telRL (TelN), loxP (Cre) and FRT (Flp) sequences in non-binding regions of pal, and SV40 enhancer sequences that flank pal on either side to enhance nuclear translocation (FIG. 2B). The rationale behind the multi-target sequence composition of SS was to allow the same parent plasmid to be passed through different R-cells to generate either lcc or ccc conformation of the minimal expression cassette. The pNN9 (5.6 kb) plasmid was used to confirm that controlled production of recombinase from R-cells was associated with controllable recombinase enzymatic activity, by examining the ability of R-cells to convert plasmids carrying the SS sites to the appropriate mini lcc (Tel) or mini ccc (Cre) conformation. The $SS^+$-derivative (pNN9; Table 1) was passaged through Tel or Cre R-cells at optimized conditions and formation of mini lcc or mini ccc vectors was assessed during the one-step in vivo processing and amplification protocol (FIG. 3A). By flanking the minimal gene of interest (GOI) with two SS, it was expected that the GOI (2.4 kb) would be excised for easy separation from the remaining prokaryotic backbone (3.2 kb) parental DNA, including the origin of replication and $Ap^R$ marker at temperatures inducing recombinase expression (FIG. 3B). Recombinase activity on pNN9 was evident when the plasmid was processed at 42° C. where R-cell recombinase expression was "on". No $SS^+$ plasmid processing was evident at 30° C. when expression was "off", or with the parent $SS^-$ controls under all tested conditions. Optimal linearization conditions for pNN9 were conducted in both Tel and TelN cells and pNN9 processed products were extracted and analyzed. These findings indicate that Tel is active upon $pal^+$-constructs in vivo and that the modification of pal target site through the addition of loxP, FRT, and telRL minimal target sequences into non-binding regions of the full 142 bp pal target site does not abrogate Tel-pal functionality.

Integration of Lcc DNA into the Chromosome Results in Loss of Cell Viability

Figure 4:
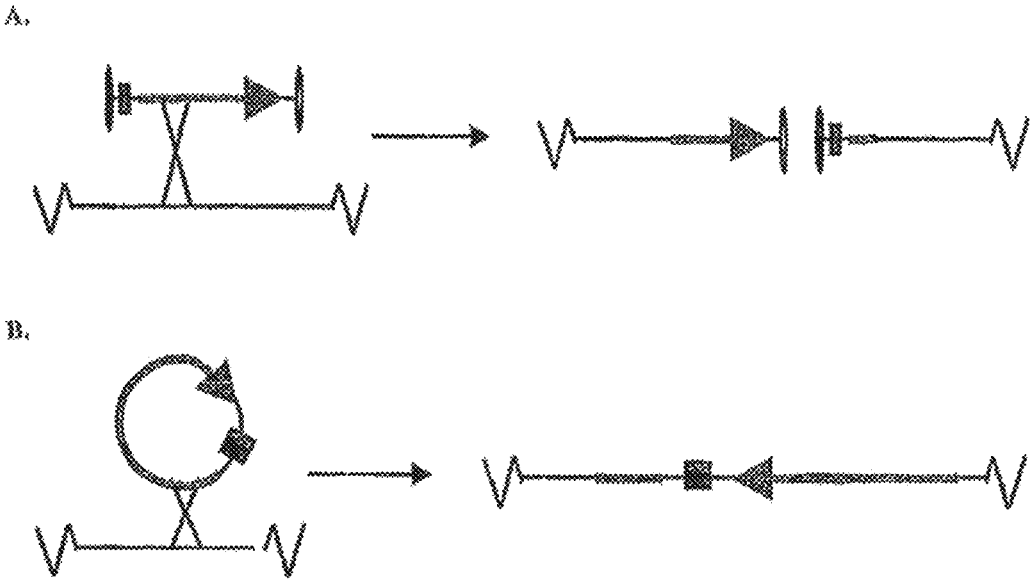
FIG. 4. Schematic representation of lcc vector integration events. A mini-vector that undergoes a single recombination event with the host chromosome is rare due to removal of all elements except the cistron containing the gene of interest expression cassette and the flanking Super Sequence sites. A. A mini ice vector integration event results in chromosomal disruption, whereby the chromosome cannot be replicated or segregated and the cell cannot divide; B. A mini ccc vector can integrate into a non-essential region of the host chromosome without disrupting it and the cell continues to divide with the insertion.

It was then determined whether or not a single crossover recombination event integrating a linear pDNA vector with covalently closed ends into a host cell chromosome would disrupt the chromosome and kill the cell (FIG. 4). To assess the outcome of linearizing the E. coli chromosome by lcc DNA integration, an in vivo approach was employed by exploiting λ and Φ80 Int-att site-specific recombination systems in a $Rec^+$ background. To target the chromosome, an integrating plasmid that carries the λ attP target site of the λ integrase and an R6K origin was used as it is only capable of replication in the presence of π (encoded by R6K pir gene), which is absent from all R-cells. As such, the plasmid is either integrated or rapidly lost from the growing cell population. An SS was incorporated into the plasmid vector to change vector conformation from ccc to lcc in the presence of TelN or Tel in R-cells. Using this system, integration efficiency was assessed following transformation of parent, Tel or TelN-cells by $SS^-$ and $SS^+$ plasmids under conditions induced or repressed for recombinase expression in R-cells. A ccc λ or Φ80 $attP^+$-$SS^+$ plasmid that is taken up by the cell expressing λ or 480 int, respectively, and producing Tel or TelN, should be altered from ccc to lcc conformation. Upon Int-mediated all-specific chromosomal integration, the recombination of lcc should disrupt the chromosome. And, as unintegrated plasmids are incapable of replication, they would be rapidly lost from the cell population.

The integration frequency (IF) of attP λ $SS^+$ plasmids into induced Tel-cells was more than $10^5$-fold lower than that seen for the $SS^-$ counterpart or the $SS^+$ plasmids in parent W3110 cells (Table 2). TelN-cells did not demonstrate nearly as strong an effect, whereby IF compared to the wild type cells was 50-fold lower, and only 25-fold lower versus integration of the SS⁻ derivative. Up to 20 survivor isolates from both TelN and Tel-cells were studied by PCR for evidence of chromosomal linearization, and it was found that 100% of tested survivors possessed intact (unlinearized) plasmid. These findings are likely due to the higher efficiency of Tel-pal system in formation of an lcc product as compared to TelN acting on the minimal telRL target site encoded within the SS.

TABLE 2

Linear covalently closed (lcc) vector confers reduced integration frequency.

| R-cell [1] | Plasmid SS (+/−−) [2] | Integration Frequency [3] |
|---|---|---|
| Cre | — | 0.76 |
| Cre | + | 0.005 |
| TelN | — | 0.51 |
| TelN | + | 0.02 |
| Tel | — | 1.0 [4] |
| Tel | + | $1.03 \times 10^{-5}$ |

[1] R-cells are all W3110 derivatives expressing recombinase gene at fully induced temperature where possible and carrying pAH153 plasmid induced for λ int expression

[2] pAH20 plasmid encoding λ attP

[3] Mean of minimum 3 trials. IF is expressed as fraction of integration frequency of parent strain, W3110

[4] IF compared to W3110 exceeded 1.0 (1.05).

Chromosomal linearization was then studied by constructing $SS^+$ or $SS^-$ integrants using the same λ and Φ80 Int-attP plasmid integration system. Unlike the previous experiment, this time, rather than assessing the number of integrants formed in the presence of the linearizing recombinase, the plasmid was first stably integrated into the chromosome before inducing recombinase expression. Cells carrying the integrated $SS^+$ or $SS^-$ vector were maintained under repressed tel and telN conditions (30° C.) and several isolates were assessed for integration of single versus multiple copies of vector by PCR. In all cases, single integration events represented the majority of recombinants for both vectors (56.5-100%). Multiple copy integrants were not studied further and discarded.

To determine the fate of cells upon linearizing/disrupting the E. coli chromosome, λ site-specific $SS^-$ and $SS^+$ integrants were incubated under conditions that provide none to very low (30° C.) or full (42° C.) expression of the recombinase, then cell viability was measured (Table 3). Under repressed conditions (30° C.), all recombinant cells retained near full viability regardless of the presence or absence of the SS integrated in the chromosome. However, upon shifting temperature to 42° C. and inducing expression of Tel or TelN, recombinants that carried $SS^+$ showed dramatically reduced viability. And, in both systems, Tel-cells resulted in approximately 5-fold greater killing than that seen in TelN-cells. Interestingly, the killing effect of $SS^+$ vector in Φ80 attB site was about 10-fold lower than was observed when integrated into λ attB site. This finding suggests that positioning of the attB site may influence the viability of cells with linear chromosome.

TABLE 3

Recombinase-mediated linearization of the chromosome results in cell killing.

| R-cell [1] | Integrated Plasmid SS (+/−) [2] | | Cell viability following induction [3] 30° C. | 42° C. |
|---|---|---|---|---|
| TelN | — | λ | 0.8 | 0.6 |
| TelN | + | λ | 1.0 | $5.7 \times 10^{-4}$ |
| TelN | — | Φ80 | 0.8 | 0.4 |
| TelN | + | Φ80 | 1.0 | $5 \times 10^{-3}$ |
| Tel | — | λ | 1.0 | 1.0 |
| Tel | + | λ | 1.0 | $1.3 \times 10^{-4}$ |
| Tel | — | Φ80 | 1.0 | 0.8 |
| Tel | + | Φ80 | 1.0 | $1.1 \times 10^{-3}$ |

[1] R-cells are all W3110 derivatives cured of pAH153 plasmid during construction stage and confirmed for single integration event by PCR

[2] pAH20 plasmid encoding λ attP grown and prepared under minimal inducing conditions (30° C.)

Figure 5:
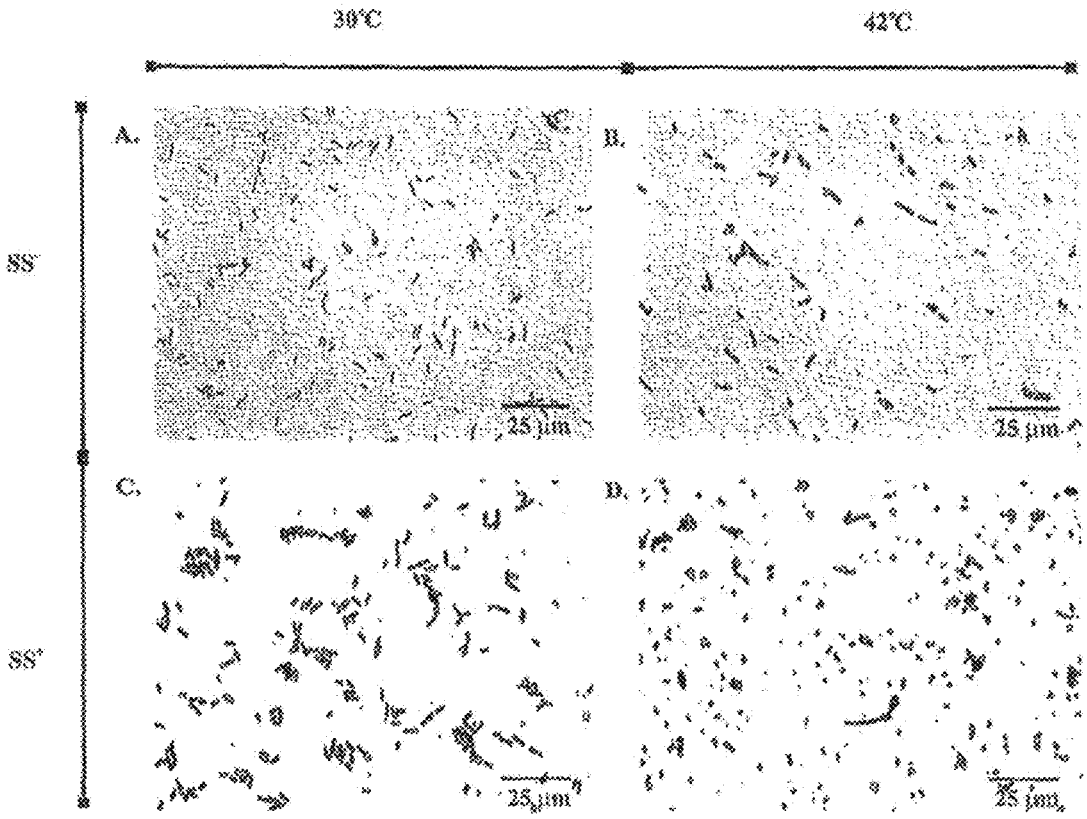
FIG. 5. Effect of Tel-mediated chromosomal disruption on cell morphology. Tel-mediated disruption of the host chromosome results in a contracted cellular morphology. Cells possessing an integrated plasmid that was $SS^+$ ($pal^+$) or $SS^-$ ($pal^-$) were grown in LB at 30° C. to early log phase $A_{600}$=0.2, then were divided in two tubes and grown at 30° C. or 42° C. for 1 h to $A_{600}$=0.8. Bacterial smears were then prepared on the slide and heat fixed and gram stained. Pictures of bacteria were taken at 1000× magnification. A. $SS^-$ integrants at 30° C. where tel expression is repressed in Tel-cell; B. $SS^-$ integrants at 42° C. where tel is induced by the pal target site is absent; C. $SS^+$ integrants at 30° C. where pal target site is present but tel expression is repressed; D. $SS^+$ integrants at 30° C. where tel is induced and free to act on the chromosomally integrated pal target site.

[3] Average of minimum 3 trials. Viability is expressed as a fraction of colonies counted under non-induced (25° C.) conditions Visualization of Cells Upon Induction Wild type and Tel-cells carrying chromosomally integrated $SS^+$ or $SS^-$ plasmids were gram stained and visualized under conditions repressed (30° C.) versus induced (42° C.) for tel recombinase expression to investigate cell morphology as a result of chromosomal disruption (FIG. 5). At 42° C., only Tel-cells $SS^+$ integrants demonstrated a highly contracted and irregular morphology compared to $SS^-$ cells, or $SS^+$ cells grown at 30° C., repressed for tel expression. Ten $Tel^+/SS^+$ colonies that grew at 42° C. were screened for linearization by PCR and it was found that all of the colonies showed an unlinearized $SS^+$ plasmid insert (data not shown). Surviving colonies were, however, very small compared to their $SS^-$ counterpart or the wild type parent, and retained this morphology whether grown under inducing or repressed conditions. The length of 400 randomly selected cells was averaged. It was noted that the $SS^-$ controls were similar at both 30° and 42° C. with a normal average length for log phase E. coli in rich medium, measuring 3.9±0.4 and 3.9±0.6 μm, respectively. In contrast, cells, possessing the chromosomally integrated SS site, were much smaller at 42° C., where tel expression was fully induced, averaging only 1.2±0.2 μm in length. In contrast, a small proportion of these cells (1.5%) were filamentous. This may be attributed to replication delay or inhibition in these cells. At 30° C., where tel expression was repressed, cells were considerably larger at 3.0±0.8 μm but there was a much greater variability in size between cells ranging from 1.2 to 4 μm. This variability could be the consequence of leaky expression of tel due to incomplete repression of the CI[Ts]857 repressor at 30° C.

Discussion

The mini pDNA vector production system, described here, is an in vivo platform to generate high quality bacterial sequence-free mini plasmid vectors in both lcc and ccc topology. Modified mini vectors can be purified directly from engineered E. coli cells (R-cells) using standard plasmid isolation methods, and without the need for digestion, ligation, and gel purification. R-cells were designed and optimized to chromosomally encode specific recombinases under control of a strong promoter. However, since strong promoters impart metabolic burden on the host cell, where protein production may occur at the expense of cell growth, a thermally-regulated promoter system was employed that circumvents any potential toxicity, metabolic stress or recombinase interference that might arise from the use of chemical-mediated induction strategies. As such, the production of mini pDNA vectors was optimized through simple control over manufacture temperature using the λ CI[Ts]857 oL-pL expression system. Various modifications to the parent vector construct by simple passaging through different R-cells was made possible by the insertion of the unique multi-target sequence (Super Sequence) described for the first time here. The Super Sequence inserts the cleave joining multi-target site for TelN, Cre and Flp within the non-coding regions of the minimal 142 bp pal sequence required for in vivo processing by Tel. The retained activity of Tel in processing this site indicates that the replacement of non-coding regions within the pal site of PY54 does not appear to compromise cleave joining activity.

Mini linear covalently closed (lcc) vectors, devoid of parental prokaryotic genetic elements were successfully generated in vivo exploiting the bacteriophage PY54-derived protelomerase recombination system. The mini vector produced via this system is a stable linear DNA expression cassette with covalently closed ends that confers a safer alternative nonviral DNA vector with robust applications including gene therapy and vaccination. Application of pDNA vectors in naked, lipoplexed, or polyplexed form for gene transfer conventionally employs plasmids designed either to administer genes coding for therapeutic proteins, antigens, or antibodies into a given organism; or introduce a correct gene into a host cell to replace the mal- or non-functional allele. Derived from conventional plasmid DNA vectors, bacterial sequence-free mini vector derivatives provide superior alternatives to traditional plasmids.

Conclusion

Mini lcc vector constructs were generated in vivo exploiting the bacteriophage PY54-derived Tel/pal recombination system in a conditional recombinase expression system. The lcc mini vectors provide a safer alternative to conventional DNA vectors without compromising utility. In addition to a unique multi-target sequence, each vector is equipped with two SV40 enhancer sequences at the two covalently closed ends of the linear vectors to facilitate the nuclear uptake and enhance the transfection efficiency and expression of the GOI.

Example 2

Materials and Methods

Strains and Plasmids

E. coli K-12 strains were used to generate recombinant cell constructs and to employ JM109 as hosts for plasmid construction and amplification. A list of bacterial and phage strains used in this study are shown in Table 1 above and Table 4 below.

TABLE 4

| Plasmids. Plasmids | | |
|---|---|---|
| pUC57-SS | Multi target site "SS" ($Ap^R$) | GeneScript |
| pcDNA5/FRT | Flp-In Integrating vector frt-hyg-pCMV::MCS-BGHpA ($Ap^R$ $Hyg^R$) | Invitrogen |
| pcDNA5/FRT/CAT | Flp-In positive control Integrating vector frt-hyg-pCMV::MCS::CAT-BGHpA ($Ap^R$ $Hyg^R$) | Invitrogen |
| pOG44 | Flp-In Integrase vector ($FLP^+$)($Ap^R$) | Invitrogen |
| pcDNA $3.1^{(+)}$ | pCMV::MCS-BGHpA ($Ap^R$ $Neo^R$) | Invitrogen |
| pcDNA $3.1^{(+)}$/CAT | pCMV::MCS::CAT-BGHpA ($Ap^R$ $Neo^R$) | Invitrogen |
| pNN12 | pBRINT ($Cm^R$) ($SS^+$) | This study |
| pNN13 | pcDNA5/FRT ($SS^+$) | This study |
| pNN14 | pcDNA5/FRT/CAT ($SS^+$) | This study |
| pNN15 | pcDNA5/FRT ($tel^+$) | This study |
| pNN16 | pcDNA $3.1^{(+)}$($tel^+$) | This study |
| pNN17 | pcDNA $3.1^{(+)}$/CAT ($SS^+$) | This study |

[1] sequences of interest confirmed by PCR and/or sequencing

Plasmids pcDNA5/FRT, pcDNA5/FRT/CAT integrating vectors, and pOG44 integrase expressing vector were obtained from Invitrogen (Carlsbad, USA) and pGL2 expression vector was obtained from Promega (Madison, USA). Restriction enzymes and DNA modifying enzymes were obtained from New England Biolabs (Beverly, USA). HEK 293 and OVCAR-3 cells were grown in complete media (high Glucose DMEM+sodium pyruvate+GlutaMAX supplemented with 10% FBS, 100 μg/ml streptomycin, and 100 IU/ml penicillin) and (RPMI+GlutaMAX supplemented with 20% FBS, 100 μg/ml streptomycin, and 100 IU/ml penicillin), respectively. Flp-In 293 cells were grown in DMEM complete media supplemented with 100 μg/ml zeocine. The GFP expressing pVGtelRL vector (a gift from Dr. Jochen Heinrich, Germany) was used as an internal control for TE. All cell culture reagents were provided by Life Technologies (Mississauga, Canada), cell culture equipment from VWR and Fisher, and chemical reagents from Fisher and Sigma.

Construction and Characterization of Ministring DNA

The multi-purpose target site, named SS, was designed to carry two flanking 78 bp SV40 enhancer sequences to facilitate nuclear translocation and enhancing TE and moved to pGL2 vectors to generate plasmid vectors pNN7, pNN8, and pNN9. New constructs were tested and confirmed by colony PCR and analytical digestion. The CCC pVGtelRL, and pNN9 (eGFP expressing vectors with no and with four DTS, respectively) were converted to LCC pDNA, DNA minicircles or DNA ministrings by passaging 1 μg of the conventional corresponding plasmids through R-cells. R-cells were then grown on LB+Ap (100 μg/ml) to $A_{600}$=0.8 at 30° C. with aeration. To induce recombinase expression and plasmid conformational conversion, cells were collected at late logarithmic phase of bacterial growth by centrifuge at 12,000 RPM for 2 min, then the media was removed and transformed R-cells were transferred to a new culture flask with media preheated at 42° C. to conduct heat shock and to induce recombinase expression at 42° C. for 30 min at late logarithmic phase of bacterial growth, before being transferred to 30° C. overnight. Cells were then harvested and plasmid was extracted (Endotoxin-free plasmid isolation maxi kit, Omega, VWR). DNA vector topology was assayed by agarose gel electrophoresis (AGE), ethidium bromide (EtBr) staining, and analytical digestion. Standard recombinant DNA techniques were performed as described by Sambrook et al. (1989).

Transfection Efficiency Assay of Ministring DNA Vector

Cationic polymer transfection reagents (jetPRIME) were obtained from VWR and cationic lipid transfection reagents (Lipofectamine 2000, Lipofectamine LTX, and Plus reagents) were obtained from Invitrogen. For transfection using these reagents, $0.5\text{-}1\times10^6$ OVCAR-3 and $1\text{-}2\times10^6$ HEK 293 cells were seeded into six-well culture plates 24 h before transfection in complete media w/o antibiotic. One to two pmol DNA vector were mixed by lipid- or polymer-based carriers for each well. 1 h before transfection, culture medium was replaced to serum-free medium. DNA and transfection reagent were then mixed with 0.5 ml serum-free OptiMEM culture medium in separate tubes and incubated for 10 min at room temperature. Cationic complex jetPRIME or Lipofectamine solution was added to the DNA solution, mixed by vortexing, and incubated for an additional 30 min at room temperature. Medium culture was removed from the plate and the mixture of transfection-reagent and DNA was added dropwise. The culture was centrifuged for 5 min at 200 rpm at room temperature. The plates were incubated at 37° C. and after 2 h, six-well plates were filled up to 2 ml on complete medium w/o antibiotic. Transfection efficiency (TE) was controlled after 48 h. Ratios of DNA and transfection reagent were optimized for the two cell lines and for the LCC pDNA. Different combinations of transfection reagent (1-10 μl cationic complex, corresponding to 1-2 pmol pDNA) were tested.

Flow Cytometry

TE was determined 48 h after transfection by flow cytometry using an Epics XL (Biology, University of Waterloo). Cells were trypsinized 48 h after transfection, washed with PBS, and counted. Data were collected from $10^6$ cells. Ten microliters of propidium iodide (PI), 20 mg/ml (Sigma-Aldrich, Canada) was added to measure toxicity by detecting necrotic cells. Cells with no transfection and cells transfected only with transfection reagent served as PI and mock transfection control, respectively. Cells transfected by 1 pmol of pVGtelRL served as GFP control. Indicator eGFP expression levels were calculated by multiplying the mean relative fluorescence values of transfected cells by the percentage of transfected cells. This parameter is considered to be directly proportional to the total amount of produced transgene product. Apoptosis was detected using the AnnexinV/PI staining assay. Annexin V binds to plasma membrane associated with phosphatidyl serine, and PI intercalates with DNA only by entering the cell through a broken plasma membrane. Flow cytometry readings of $Annexin^+/PI^+$, $Annexin^+/PI^-$ and $Annexin^-/PI^-$ indicate a viable cell, early apoptotic cell and dead cell, respectively. Flow cytometry was performed using a "Guava EasyCyte Flow Cytometer" (Millipore, Billerica, Mass., USA).

Statistical Analysis

One way ANOVA was used to analyze statistical significance. A P value of ≤0.05 was considered significant. Each standard error bar represents a minimum of three separate transfections.

DNA Vector Labeling and Real Time Assay of Intercellular Kinetics of Ministring DNA Modified pGL2 pDNA expressing eGFP (pNN7) with no DTS and (pNN9) flanking two SS and four DTS, enhanced ministring and enhanced minicircle egfp expression DNA vectors, were labeled with the Label IT® Tracker Reagent Cy5 (Excitation wavelength 649 nm and Emission wavelength 670 nm from Mirus) at a weight ratio Cy5:DNA of 0.5:1 and incubated for 3 h at 37° C. Unreacted Cy5 was removed from the labeled DNA by ethanol precipitation. Labeled DNA was resuspended in 10 μl sterile nuclease-free water. Concentration of the purified, labeled DNA was measured by NanoDrop spectrophotometer and the integrity of labeled DNA was quantified by AGE before and after labeling with and without EtBr staining in order to confirm the direct and non-destructive nature of the labeling reaction. Labeled DNA was protected from light. $10^4$ OVCAR-3 or $10^5$ HEK 293 cells were seeded on non-coated or collagen coated 35 mm glass bottom plates, respectively, in their complete media, such that their confluency was approximately 60% at the time of imaging and treated by 0.5 μM SYTO80 nuclear stain 1 h prior to transfection. These cells were transfected (Lipofectamine) by 0.5 μg of labeled DNA vectors pNN7, pNN9, ministring and "minicircle" egfp expression DNA vector, and pVGtelRL as an internal eGFP expression control. Lipoplexed DNA was prepared by diluting 3:1 ratio of Lipofectamine 2000:labeled DNA in serum-free OptiMem media, incubated for 30 min at room temperature prior to transfection. Transfected cells were monitored for DNA vector diffusion rate into the cytoplasm to nuclear membrane at 3 h and 5 h post-transfection and pictures were obtained by 2D Z stack with dual channel imaging of SYTO Orange and Cy5 scan to record localization of DNA vector with respect to the nucleus.

Construction and Characterization of LCC Integrating pDNA Vectors

To construct modified integrating vectors, the SS fragment was moved from pUC57 into MCS of pBRINT ($Cm^R$) plasmid by BamHI and EcoRI to generate pNN12, and moved from pNN12 by BamHI and XhoI into MCS of pcDNA5/FRT and pcDNA5/FRT/CAT vectors (Invitrogen) to produce pNN13 and pNN14, respectively (Table). New constructs were tested and confirmed by colony PCR and analytical digestion. One microgram of supercoiled CCC pNN13 and pNN14 constructs were electroporated into W3NN R-cells ($tel^+$) and grew on LB+Ap (100 μg/ml) to $A_{600}$=0.8 at 30° C. with aeration. To induce recombinase expression and plasmid conformational conversion, transformed cells were heat shocked to induce the Tel recombinase expression at 42° C. for 30 min at late logarithmic phase of bacterial growth, before being transferred to 30° C. overnight. Cells were then harvested and the plasmid was extracted (Omega maxi plasmid extraction kit, VWR). LCC pDNA topology was assayed by AGE, EtBr staining, and analytical digestion.

Assessing Fate of LCC DNA Vector Chromosomal Integrant Cells $5\times10^5$ Flp-In 293 cells/well were seeded in a 6-well plate with 2 ml complete DMEM media w/o antibiotic, such that their confluency was approximately 80% at the time of transfection. Cells were cotransfected by 0.3 μg of CCC and LCC forms of pNN13 (pcDNA5/FRT+SS) and CCC and LCC forms of pNN14 (pcDNA5/FRT/CAT+SS) with a 9:1 (integrase:pDNA) molarity ratio of pOG44:integrating pDNA vector. pDNA vectors were mixed by Lipofectamine LTX and Plus reagents to the 1:3 DNA:lipid and 1:0.5 DNA:plus helper lipid, respectively, and incubated for 30 min at room temperature to produce lipoplexed DNA in serum-free OptiMem media. We included the following controls: 1) untransfected cells as a negative control; 2) pcDNA5/FRT/CAT vector as a positive control; 3) pCDNA5/FRT/GOI transfected without pOG44 to see when the selection is complete; and 4) mock transfection. 48 h post-transfection, transfected cells were collected and expanded into 100 mm plates contained complete DMEM media with no zeocin, in such way that they were not more than 25% confluent. After cells were attached to the new plates, hygromycin was added to the final concentration of 200 μg/ml. Selection and expansion of stably integrated cells were performed in the presence of hygromycin for 3 to 5 weeks post-transfection. Integrated cells were tested for lack of 1-galactosidase activity using the B-gal staining kit protocol from Invitrogen. CAT expression level was measured following CAT ELISA protocol from Roche. Zeocin sensitivity test was performed by growing cells in a gradient concentration of zeocin 0, 25, 50, 75, and 100 μg/ml. To further verify that the site-specific recombination was occurring at the frt site, genomic DNA isolated from $Hyg^R$, $Zeo^S$, $B\text{-}Gal^-$ Flp-In::GOI cells was subjected to PCR with pCMV-F and BGH-R specific primers that would only amplify at site of integration. New cells were expanded as Flp-In::cat, Flp-In::SS-cat, and Flp-In::SS.

Viability Assay of LCC DNA Integration

Integrant cells ($10^6$) $Hyg^R$, $Zeo^S$, B-Gal$^-$ CCC and LCC were collected and washed two times by cold PBS. 250 μL of the Annexin V and PI solution was added and incubated in the dark for 15 min at room temperature and then measured by flow cytometry. Data were normalized by three controls: unstained non-integrated cells, non-integrated cells stained with only Annexin V, and non-integrated cells stained with only PI (ApoAlert Annexin V Apoptosis Kit from Clontech).

Results

Ministring DNA Vectors Exhibit Higher Transfection Efficiencies

Figure 6:
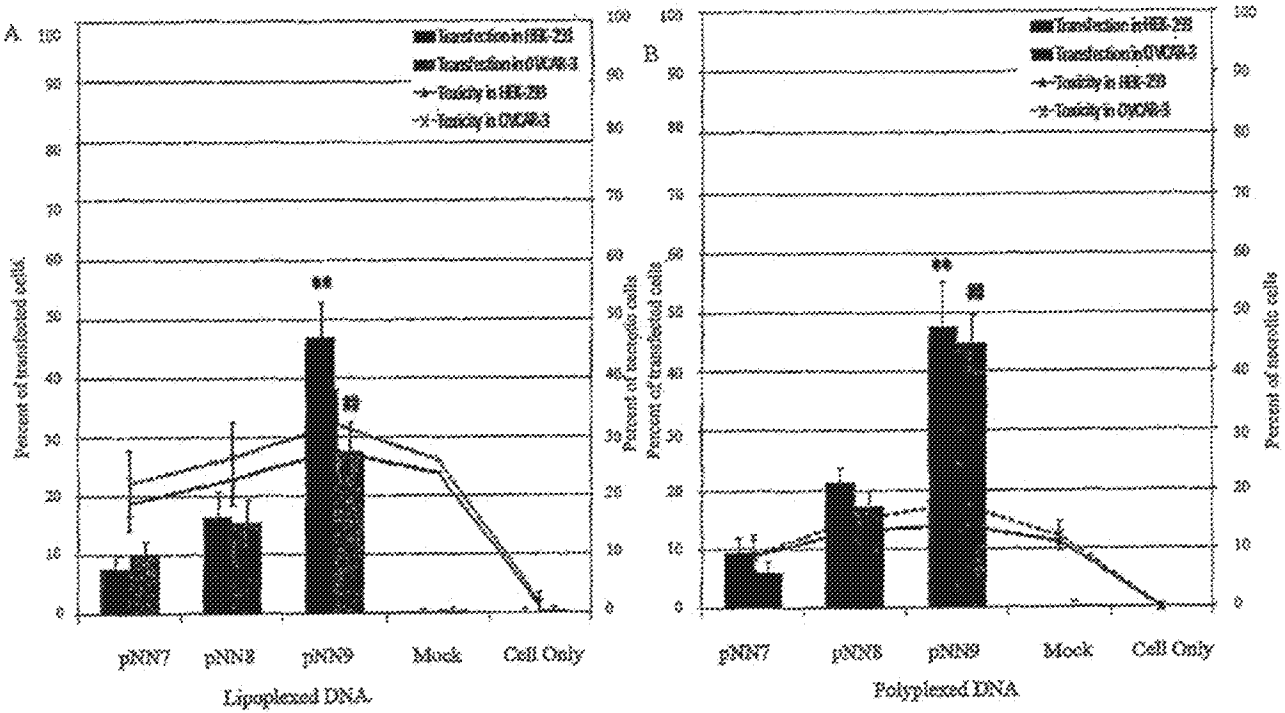
FIG. 6 graphically illustrates the effect of SV40 enhancer sequence on transfection efficiency in lipoplexed (A) and polyplexed (B) DNA.

We previously constructed a pGL2 (Promega) expression vector derivative that expressed eGFP under the control of a SV40 strong promoter (pNN7). Next, we made pNN8 by adding a specially designed target sequence for the Tel recombinase that is flanked on both sides by the 76 bp DTS, SV40 Enhancer sequence (SV40E), called SS, upstream of the promoter. Another SS downstream of the polyA sequence was added to construct the enhanced pNN9 that carries 4 copies of the SV40E. By examining the SV40E copy number on TE, we found that TE continues to improve with the addition of SV40E sequences. TE of pNN9 (2 SV40E) was significantly greater than that of pNN7 (no SV40E) in both slowly dividing epithelial (HEK 293) and rapidly dividing cancer (OVCAR-3) cells (FIG. 6). These results demonstrate that enhanced TE can be conferred by increasing the units of SV40E DTS on the vector to generate enhanced DNA vectors.

Figure 7:
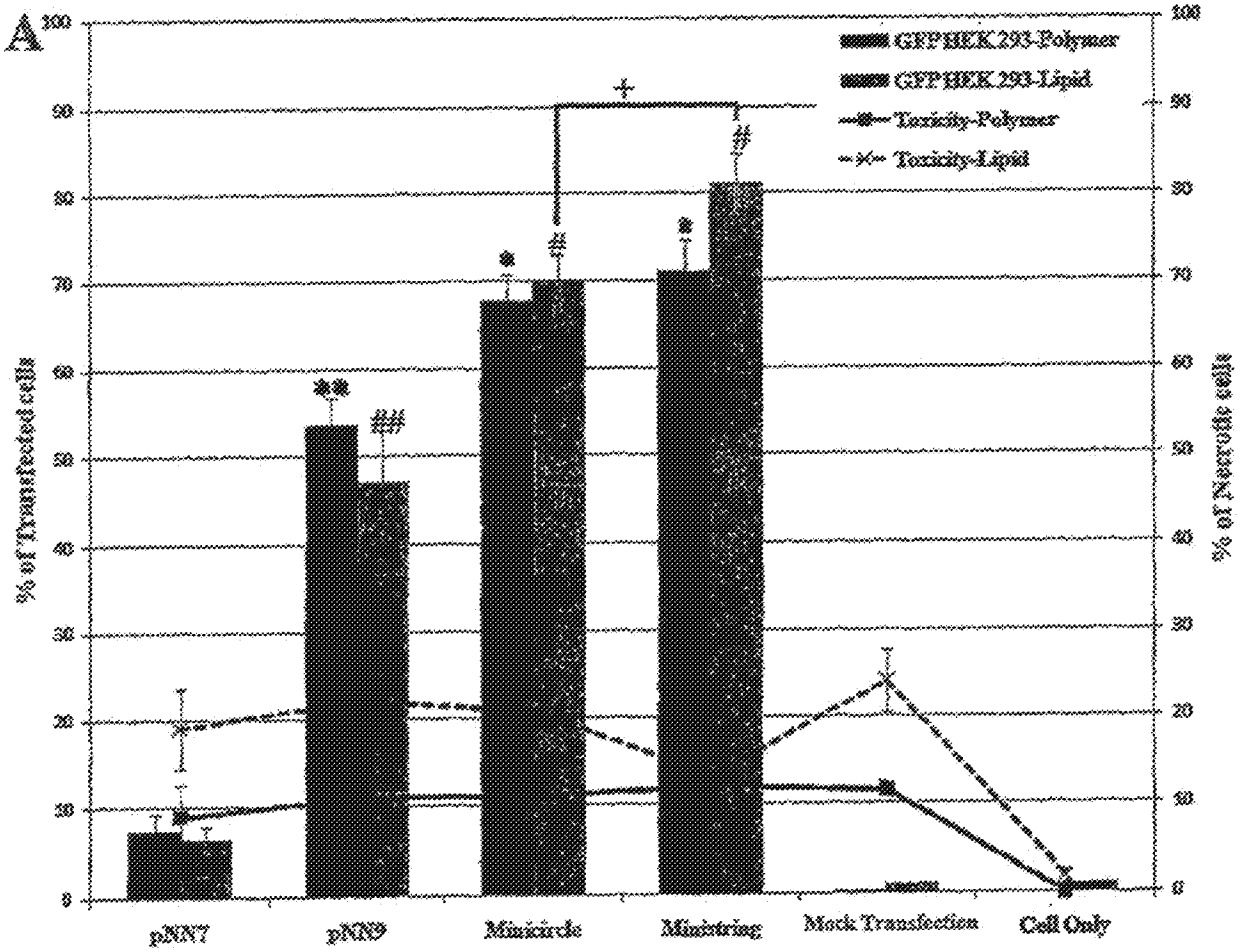
FIG. 7 graphically illustrates that enhanced mini vectors confer superior transfection efficiency in epithelial and cancer cells (A,B,C)
Figure 7:
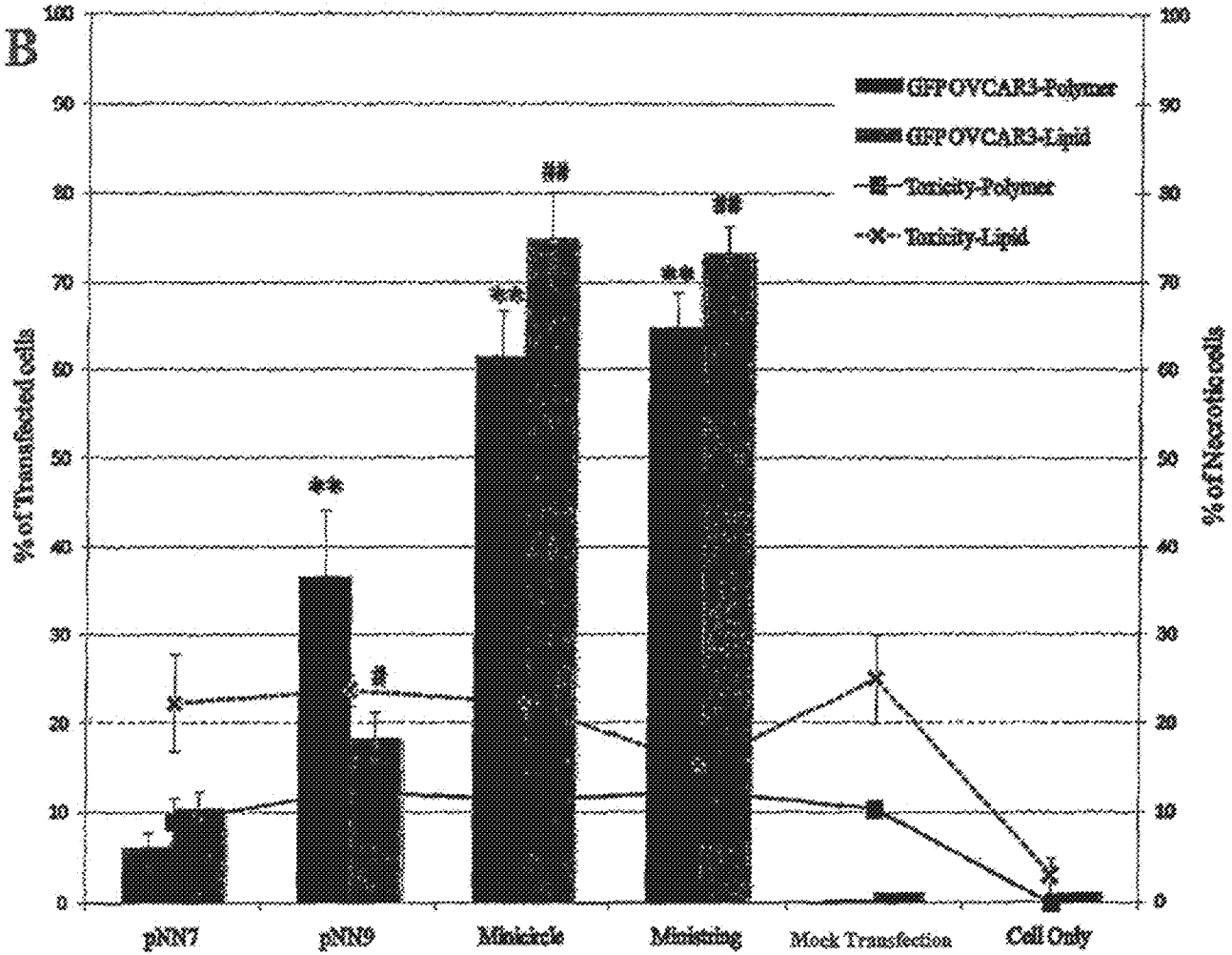
Figure 7:
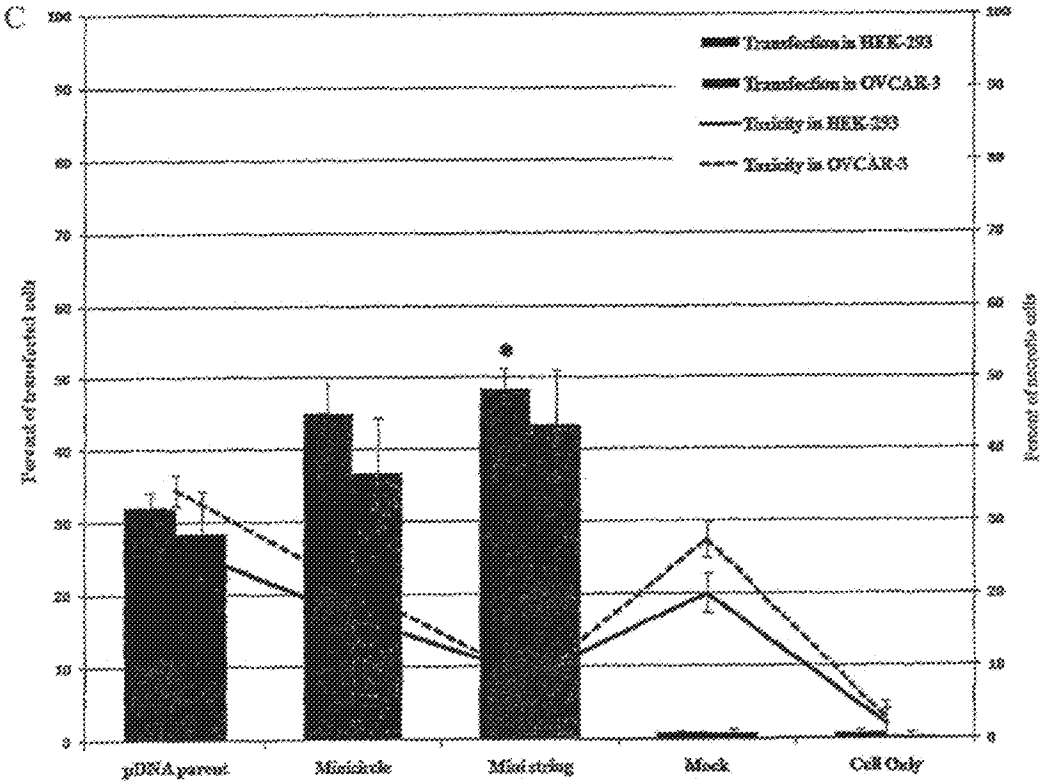

Next, parental pDNA and derivative bacterial sequence-free LCC (ministring) and CCC (minicircle) DNA vectors carrying the eGFP expression cassette were produced using a one-step in vivo linearization and separation in our recombinant E-coli (R-cell) system. In head-to-head experiments, these vectors were transfected into epithelial and cancer cells using cationic synthetic vectors, Lipofectamine (Invitrogen) or jetPRIME polymer (VWR), after measuring the eGFP expression by applying the same weight-to-weight ratios of mini DNA and parental pDNA vectors by flow cytometry. After complexing with either Lipofectamine or jetPRIME, both enhanced DNA ministrings and minicircles conferred a TE that was significantly higher than the parental pDNA controls ($p<0.001$) in slowly dividing epithelial cells (FIG. 7-A). However, lipid-complexed ministrings transfect more than 80% of the cells compared to isogenic minicircles ($p<0.05$). Similar results were observed in rapidly dividing cancer cells, although no significant difference in TE was noted between lipoplexed enhanced minicircles and ministrings (FIG. 7-B). In both cell types, lipoplexing proved to be more advantageous in the transfection of mini DNA vectors, while the opposite was true for the parent vector that benefited from polyplexing.

After complexing with Lipofectamine, by applying the same mole ratios of mini DNA and parental pDNA vectors, ministring DNA vectors conferred a significantly higher TE than the parental pDNA controls ($p<0.05$) in epithelial cells while using the same number of molecules (FIG. 7-C).

The cytotoxicity of cationic synthetic carriers complexed with the DNA vector was lower for ministring and minicircle DNA due to the lower molecular weight of mini vectors compared to their parental precursors. As a result, carrier (transfection reagent) concentration was reduced especially for ministring DNA vectors due to our optimization results indicating that LCC conformation requires 2-fold lower cationic carrier to DNA ratio for higher TE compared to the CCC counterparts (data not shown).

Enhanced Ministering DNA Vectors Exhibit Efficient Cytoplasmic Diffusion

The live vector localization via confocal microscopy was examined to determine the effect of DNA vector size and DTS availability on intercellular diffusion and distribution of enhanced DNA minicircles and ministrings. The parental precursor (pNN9) and ministring/minicircle derivatives were labeled by fluorophore prior to transfecting cancer or epithelial cells and vector intracellular location was followed using a laser confocal fluorescence microscope at variable times post-transfection. The pVGtelRL plasmid was used as a positive control, while carrier-only was the negative/mock control. Assessment of vector intercellular kinetics revealed a remarkably quicker distribution of the pDNA vectors carrying DTS sequences compared to the conventional plasmids lacking a DTS (data not shown). In addition, ministring DNA vectors, compared to isogenic minicircles and the parent precursor were more efficient at circumscribing the nucleus after 3 h suggesting better cytoplasmic diffusion is associated with the ministring DNA topology. In contrast, minicircles predominantly inhabited lysosomes at 3 h post-transfection with virtually no nuclear circumscription. Parent plasmid demonstrated poor cellular penetration and the poorest diffusion capabilities with no nuclear circumscription by 3 h.

Integration of LCC DNA into the Host Chromosome Results in Chromosomal Disruption and Cell Death We examined the safety profile of ministring DNA vectors and hypothesized that although the integration of DNA vectors into the host genome is rare, the integration of a LCC DNA vector into a human host chromosome would disrupt the chromosome at the site of integration, reducing the stability of the genome, and either killing the aberrant integrant cell or quickly targeting it for apoptosis. However, due to the circular topology, the integration of a CCC vector would not result in such disruption.

Figure 8:
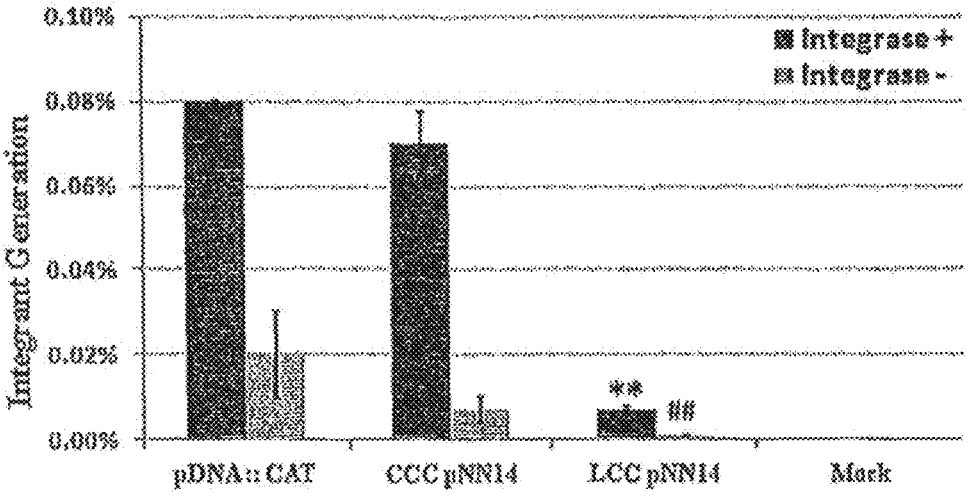
FIG. 8 shows integration frequency of LCC pDNA vectors into human cells (A/B)

To test this outcome, we forced site specific insertion of LCC or CCC DNA constructs into the human (HEK 293) genome using the commercially available Flp-In™ System (Invitrogen) that exploits the Flp-frt high efficiency recombination system (as described in Sauer, 1994). Cells that integrated the CCC or LCC DNA vector were isolated after 3 to 7 weeks. The viable IF of LCC DNA was significantly (>500-fold) lower than the isogenic CCC counterpart (FIG. 8). Any surviving LCC integrant cell colonies were isolated and found to be much smaller in size and arrested in cell division compared to a completely normal morphology and growth rate seen with CCC integrants.

Figure 9:
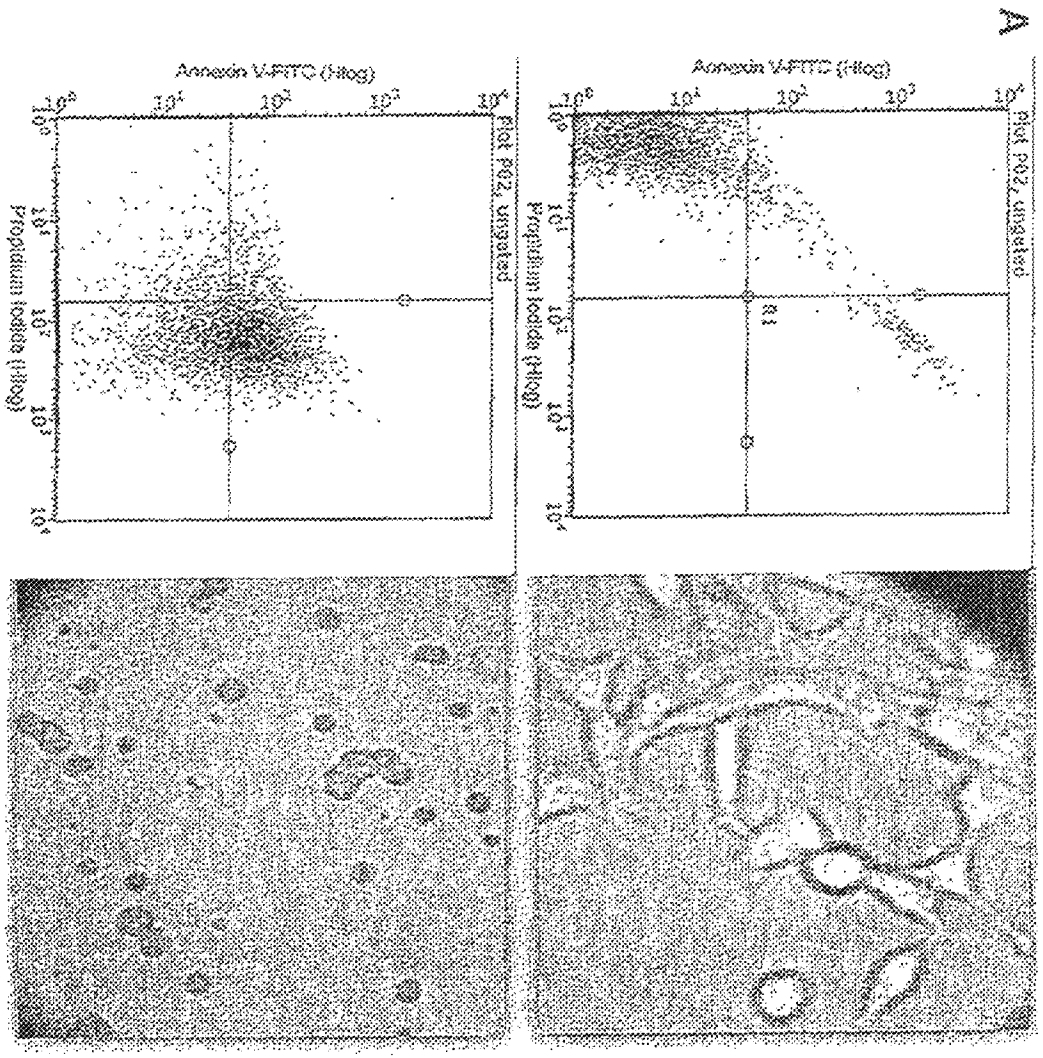
FIG. 9 graphically illustrates that LCC single cross over integration into human cell induces apoptotic cell death (A/B).
Figure 9:
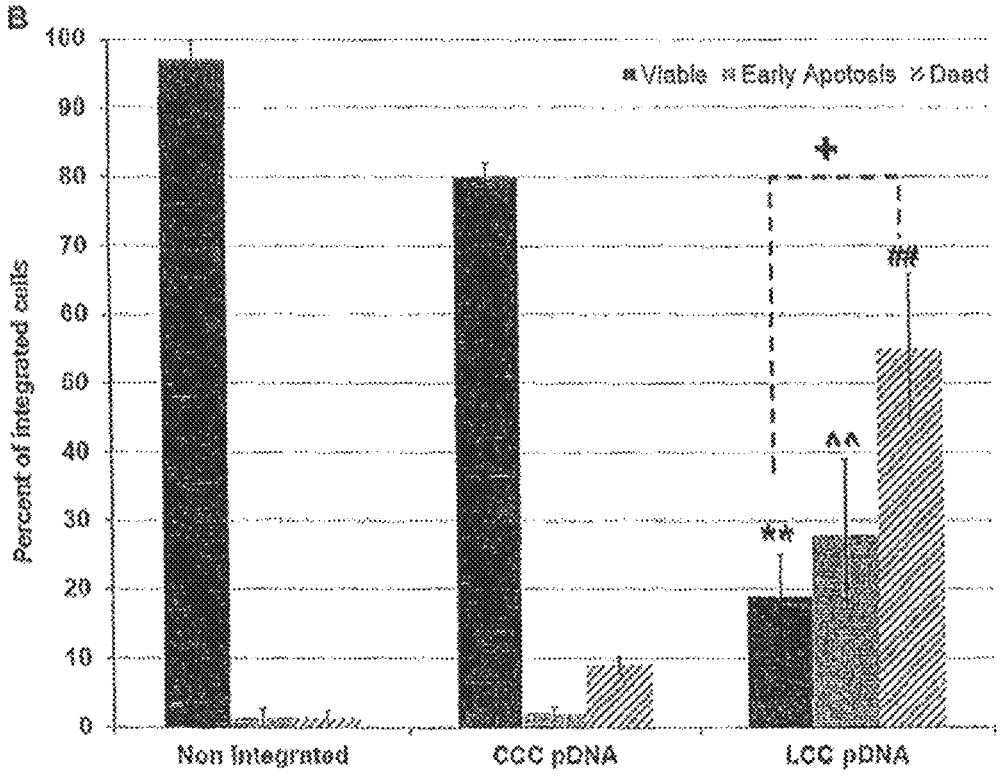

We next sought to determine whether these aberrant LCC integrant cells were viable at various stages of necrosis or apoptosis. To assess the cellular fates following LCC or CCC DNA vector integration, we employed Annexin and PI staining, and flow cytometry to distinguish early apoptotic cells (Annexin-V positive) from late apoptotic/necrotic cells (Annexin-V and PI positive) cells. More than 50% of LCC integrants were at a stage of cell death compared to a significantly healthier population of CCC integrant cells (FIG. 9).

Thus, LCC vectors such as ministrings provide a superior safety profile in terms of insertional mutagenesis. Circular DNA vectors can compromise safety as they permit unpoliced vector integration into the host DNA while LCC DNA vectors target integrant cells for cell death. The integration of an LCC DNA vector into host chromosomal DNA yields a chromosome disruption event that should separate the centromere from the telomere in a mammalian chromosome. Such genomically unstable integrant cells are arrested for growth and are targeted for apoptosis. The natural elimination of such cells prevents the propagation of potentially genotoxic integrants in the transfected cell population, thereby providing a safer option for DNA vector-mediated transgene delivery by prohibiting the manifestation of potentially oncogenic insertional mutations.

In sum, non-integrating ministring DNA vectors represent the gold standard gene transfer vectors in molecular medicine. In addition to expedited cytoplasmic diffusion and improved transfection efficiency, ministring DNA vectors offer a superior safety profile due to their lower immunogenicity and the natural elimination of the unwanted and potentially oncogenic vector insertional genotoxicity.

Example 3

Bacterial Strains and Plasmids

E. coli JM109strain was used as hosts for plasmid constructions and amplification. A list of bacterial strains and plasmids employed in this study are shown in Table 5.

TABLE 5

| Bacteria and Plasmid Vectors | | |
|---|---|---|
| Strain | Genotype or description | Source |
| | Bacteria | |
| JM109 | F', Δ (gpt-lac)0, glnV44(AS), l2, rfbC1, gyrA96(NalR), recA1, endA1, spoT1?, thi-1, hsdR17, pWM5, F128-x | New England Biolabs |
| DH5α | F-, Δ(argF-lac)169, φ80dlacZ58(M15), ΔphoA8, glnV44(AS), λ–, deoR481, rfbC1, gyrA96 (NalR), recA1, endA1, thi-1, hsdR17 | Addgene |

TABLE 5-continued

| Bacteria and Plasmid Vectors | | |
|---|---|---|
| Strain | Genotype or description | Source |
| | Plasmids | |
| pNN9 | SS-SV40P-egfp-PolyA-SS (Amp$^R$) | Nafissi and Slavcev, 2012 |
| pUC57-gRNA(C) | lacZ::grna(c)::lacZ (Amp$^R$) (gRNA sequence corresponding to target 1) | GenScript |
| pUC57-gRNA(G) | lacZ::grna(g)::lacZ (Amp$^R$) (gRNA sequence corresponding to target 2) | GenScript |
| SP-Cas9 | T7P-lac-cas9 (Amp$^R$) | Addgene |
| pBAD18 | araC-araBADP-MCS (Amp$^R$) | Guzman et al, 1995 |
| pAZ1 | araC-araBADP-grna(c) (Amp$^R$) | This study |
| pAZ2 | araC-araBADP-grna(g) (Amp$^R$) | This study |
| pAZ3 | araC-araBADP-cas9-grna(c) (Amp$^R$) | This study |
| pAZ4 | araC-araBADP-cas9-grna(g) (Amp$^R$) | This study |

Design of Target Sites and gRNA Sequences.

Cas9 endonuclease derived from S. pyogenes was selected for the experiment. The corresponding PAM sequence was NGG. Two 20 nt target sites with the following sequences were located in the pNN9 (5.6 kb) backbone region, directly upstream of the 3 nt PAM sequences: Target 1 was 5'-AGCAGAGCGAGGTATGTAGG(CGG)-3' (SEQ ID NO: 18)(located at 3449 bp-3471 bp) and Target 2 was 5'-CTCTTGCCCGGCG TCAATAC(GGG)-3' (SEQ ID NO: 19)(located at 4438 bp-4460 bp, within the ampicillin resistance gene region). The PAM sequences of each target are denoted with brackets. The gRNA sequences corresponding to target 1 and 2 were calculated using online software CRISPRdirect (Naito et al, 2015). The sequences were synthesized and inserted into the MCS of pUC57 vector.

The full gRNA sequence for target 1 (PAM: CGG) has a length of 100 bp, including the spacer and the scaffold as shown below:

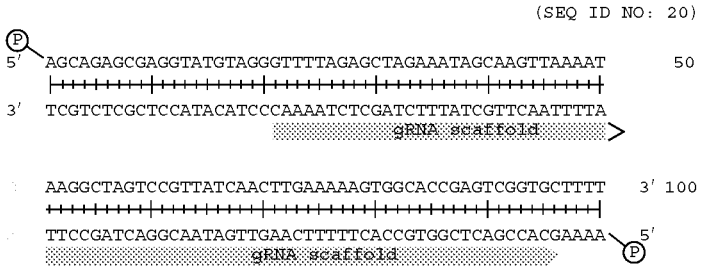

The full gRNA sequence for target 2 (PAM: GGG) has a length of 100 bp, including the spacer and the scaffold, as shown below:

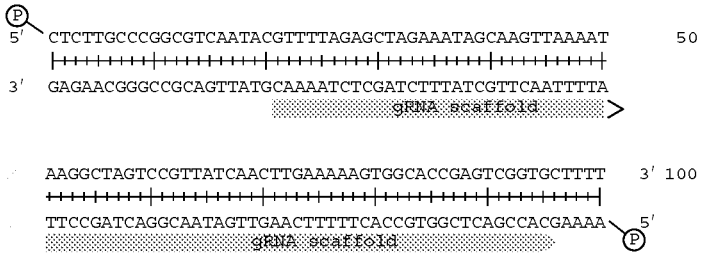

(SEQ ID NO: 21

Construction of the Expression Cassette.

To isolate the gRNA inserts, the pUC57 vectors (2.7 kb) with gRNA insertions were digested with EcoRI and SmaI (New England Biolabs), and the fragments were separated on 1.0% agarose gel. The gRNA inserts for each of target 1 and target 2 were extracted from the gel (Omega gel extraction kit), and sub-cloned into the MSC of pBAD18 (4.6 kb) under the araBAD promoter to produce recombinant plasmids pAZ1 (4.7 kb) and pAZ2 (4.7 kb), respectively. JM109 E. coli cells (50 μl of competent cells for each plasmid) were transformed by 0.1 μg of pAZ1 and pAZ2 constructs by electroporation and recovered in 500 μl SOC media in shaker at 250 rpm at 37° C. for 1 hour. 150 μl of the SOC culture was plated on LB+Amp (100 μg/ml) agar. The plates were incubated overnight at 37° C. To confirm the presence of the insert, isolated colonies of transformants were picked from the plates and incubated in LB+Amp (100 μg/ml) broth in a shaker at 250 rpm at 37° C. overnight for plasmid extraction (Omega plasmid mini kit). The plasmid extracts were confirmed by analytical digestion with EcoRI and SmaI and 1.0% agarose gel electrophoresis.

Cas endonuclease coding gene cas9 was amplified from SP-Cas9 plasmid (9.8 kb, isolated from E. coli host DH5α with Omega plasmid mini kit) using the following primers: Cas9-F 5'-AAATCCGGAGCTCAGGAGATATACCATGG-3' (SEQ ID NO: 22) (Tm 71° C.) and Cas9-R 5'-AAATT-AGAGCTCGTCACCGCCCA-3' (SEQ ID NO: 23) (Tm 71° C.). Italicized regions represent restriction sites for SacI. A two-step PCR amplification was conducted with Phusion Flash High-Fidelity PCR Mastr Mix (New England Biolabs) for 60 s at 98° C. for initial denaturation, 34 cycles of 5 s at 98° C. and 1 min at 72° C., and 1 min at 72° C. for final extension to generate cas9 (4.1 kb). PCR products were purified using Omega cycle pure kit.

Purified cas9 were sub-cloned into SacI site in the MCS of pAZ1 and pAZ2 isolated from previously transformed JM109 cells to produce recombinant plasmids pAZ3 (8.8 kb) and pAZ4 (8.8 kb). JM109 E. coli cells (50 μl of competent cells for each plasmid) were transformed by 0.3 μg of pAZ3 and pAZ4 constructs by electroporation and recovered in 500 μl SOC media in shaker at 250 rpm at 37° C. for 1 hour. 200 μl of SOC culture was plated on LB+Amp (100 μg/ml) agar. The plates were incubated overnight at 37° C., and transformants were confirmed using the same method as mentioned previously by analytical digestion with KpnI (New England Biolabs) and 0.8% agarose gel electrophoresis.

Storage of Plasmid Constructs for Future Use.

Overnight cultures of confirmed JM109 hosts of pAZ1 to pAZ4 were made in LB+Amp (100 μg/ml) broth in shaker at 250 rpm at 37° C. Sub-cultures were made by diluting the overnight cultures 1:50 into fresh LB+Amp (100 μg/ml) broth and incubating in shaker at 250 rpm at 37° C. until log phase was reached (O.D.=0.4-0.5). 1 mL of each sub-culture was mixed with 1 mL of 50% glycerol into a screw top tube and stored in −80° C. freezer.

Results and Discussion

Recombinant plasmids pAZ3 and pAZ4 were constructed that carry the cas9 gene and gRNA sequence under control of the araBAD promoter which can be induced by the activator arabinose. The plasmid constructs were each transformed into JM109 by electroporation, and the transformation efficiencies were calculated (Table 6).

TABLE 6

Transformation Efficiencies of Recombinant Plasmids into *E. coli* JM109 with Electroporation

| Recombinant Plasmids | Transformation Efficiency |
|---|---|
| pAZ1 | $1.2 \times 10^{-3}$ |
| pAZ2 | $1.4 \times 10^{-3}$ |
| pAZ3 | $4.6 \times 10^{-4}$ |
| pAZ4 | $6.2 \times 10^{-4}$ |

The pAZ1 and pAZ2 constructs were confirmed by analytical restriction enzyme digest with EcoRI and SmaI. Similarly, pAZ3 and pAZ4 were tested by analytical restriction enzyme digest with KpnI.

Thus, a CRISPR/Cas9 purification system for DNA ministring production platform was confirmed, the results showing that inducible araC-pBAD expression cassettes for Cas9 and gRNA were successfully established in pAZ3 and pAZ4 plasmid constructs. The expression cassettes are sub-cloned into pAH vectors for integration into the W3NN genome. Efficiency of the purification system is tested either in plasmid form or after integration.

While the araC-pBAD expression system was exemplified above, other expression systems for the Cas9 and gRNA may also be utilized. In another embodiment, the YF1/FixJ expression system characterized by Ohlendorf et al. (2012) Journal of Molecular Biology, 416(4), 534-542). In this system, gene expression from the pFixK2 promoter is activated by the presence of blue light. This may provide another layer of biosafety for the purification system as its induction does not require addition of any chemical reagent.

In another embodiment, an expression system is utilized in which the cas9 and gRNA coding sequence are under the control of two separate promoters.

SEQUENCE LISTING

```
<160> NUMBER OF SEQ ID NOS: 23

<210> SEQ ID NO 1
<211> LENGTH: 54
<212> TYPE: DNA
<213> ORGANISM: Artificial Sequence
<220> FEATURE:
<223> OTHER INFORMATION: telRL site

<400> SEQUENCE: 1

tatcagcaca caattgccca ttatacgcgc gtataatgga ctattgtgtg ctga          54


<210> SEQ ID NO 2
```

<211> LENGTH: 42
<212> TYPE: DNA
<213> ORGANISM: Artificial Sequence
<220> FEATURE:
<223> OTHER INFORMATION: pal site

<400> SEQUENCE: 2 acctatttca gcatactacg cgcgtagtat gctgaaatag gt 42

<210> SEQ ID NO 3
<211> LENGTH: 22
<212> TYPE: DNA
<213> ORGANISM: Artificial Sequence
<220> FEATURE:
<223> OTHER INFORMATION: K02 telRL site

<400> SEQUENCE: 3 ccattatacg cgcgtataat gg 22

<210> SEQ ID NO 4
<211> LENGTH: 33
<212> TYPE: DNA
<213> ORGANISM: Artificial Sequence
<220> FEATURE:
<223> OTHER INFORMATION: loxP site

<400> SEQUENCE: 4 taacttcgta tagcatacat tatacgaagt tat 33

<210> SEQ ID NO 5
<211> LENGTH: 34
<212> TYPE: DNA
<213> ORGANISM: Artificial Sequence
<220> FEATURE:
<223> OTHER INFORMATION: FRT site

<400> SEQUENCE: 5 gaagttccta ttctctagaa agtataggaa cttc 34

<210> SEQ ID NO 6
<211> LENGTH: 100
<212> TYPE: DNA
<213> ORGANISM: Artificial Sequence
<220> FEATURE:
<223> OTHER INFORMATION: phiC31 attP site

<400> SEQUENCE: 6 cccaggtcag aagcggtttt cgggagtagt gccccaactg gggtaacctt tgagttctct 60 cagttggggg cgtagggtcg ccgacaygac acaaggggtt 100

<210> SEQ ID NO 7
<211> LENGTH: 100
<212> TYPE: DNA
<213> ORGANISM: Artificial Sequence
<220> FEATURE:
<223> OTHER INFORMATION: lambda attP site

<400> SEQUENCE: 7 tgatagtgac ctgttcgttg caacacattg atgagcaatg ctttttttata atgccaactt 60 tgtacaaaaa agctgaacga gaaacgtaaa atgatataaa 100

<210> SEQ ID NO 8
<211> LENGTH: 31
<212> TYPE: DNA
<213> ORGANISM: Artificial Sequence <220> FEATURE:
<223> OTHER INFORMATION: primer

<400> SEQUENCE: 8 gcggatcctg ggttacttta atttgtgtgt t 31

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9 cgctcgagtt actccatatt ttcagtccat gcttgt 36

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10 atcggatccc gatatccaga gacttagaaa cggg 34

<210> SEQ ID NO 11
<211> LENGTH: 39
<212> TYPE: DNA
<213> ORGANISM: Artificial Sequence
<220> FEATURE:
<223> OTHER INFORMATION: primer

<400> SEQUENCE: 11 atataaagct tcttttagct gtagtacgtt tcccatgcg 39

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12 ggaattccgg tcgctggcgt ttctatgac 29

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13 cgctcgagtg aatattagtg cttacagaca g 31

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14 tccccgcgga gctatgacca tgattacgaa ttgc 34

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15 ggactagtcc ccattcaggc tgcgcaactg ttg 33

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16 gctctagagc aggctgcgca actgttggga ag 32

<210> SEQ ID NO 17
<211> LENGTH: 10
<212> TYPE: DNA
<213> ORGANISM: Artificial Sequence
<220> FEATURE:
<223> OTHER INFORMATION: palindromic sequence

<400> SEQUENCE: 17 tacgcgcgta 10

<210> SEQ ID NO 18
<211> LENGTH: 23
<212> TYPE: DNA
<213> ORGANISM: Artificial
<220> FEATURE:
<223> OTHER INFORMATION: Cas 9 target sequence

<400> SEQUENCE: 18 agcagagcga ggtatgtagg cgg 23

<210> SEQ ID NO 19
<211> LENGTH: 23
<212> TYPE: DNA
<213> ORGANISM: Artificial
<220> FEATURE:
<223> OTHER INFORMATION: Cas9 target sequence

<400> SEQUENCE: 19 ctcttgcccg gcgtcaatac ggg 23

<210> SEQ ID NO 20
<211> LENGTH: 100
<212> TYPE: DNA
<213> ORGANISM: Artificial
<220> FEATURE:
<223> OTHER INFORMATION: gRNA sequence

<400> SEQUENCE: 20 agcagagcga ggtatgtagg gttttagagc tagaaatagc aagttaaaat aaggctagtc 60 cgttatcaac ttgaaaaagt ggcaccgagt cggtgctttt 100

<210> SEQ ID NO 21
<211> LENGTH: 100
<212> TYPE: DNA
<213> ORGANISM: Artificial

-continued

```
<220> FEATURE:
<223> OTHER INFORMATION: gRNA sequence

<400> SEQUENCE: 21

ctcttgcccg gcgtcaatac gttttagagc tagaaatagc aagttaaaat aaggctagtc     60

cgttatcaac ttgaaaaagt ggcaccgagt cggtgctttt                          100


<210> SEQ ID NO 22
<211> LENGTH: 29
<212> TYPE: DNA
<213> ORGANISM: Artificial
<220> FEATURE:
<223> OTHER INFORMATION: primer

<400> SEQUENCE: 22

aaatccggag ctcaggagat ataccatgg                                       29


<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23

aaattagagc tcgtcaccgc cca                                             23
```

We claim:

[1. A vector production system comprising recombinant cells designed to encode at least a first recombinase under the control of an inducible promoter, wherein said cells comprise an expression vector adapted to produce a bacterial sequence-free vector, said expression vector comprising an e xpression cassette, and a nucleic acid of interest flanked on either side by a target binding sequence for the Tel recombinase and integrated within non-binding regions of the Tel target binding sequence are target binding sequences for one or more additional recombinases, wherein the nucleic acid of interest encodes a nuclease genome editing system.]

[2. The system of claim 1, wherein the inducible promoter is thermally-regulated, the IPTG regulated, glucose-regulated, T7 polymerase regulated, cold-shock inducible, pH inducible, or combinations thereof.]

[3. The system of claim 1, wherein the vector comprises the target binding sequence for one or more additional recombinases selected from the group consisting of the telRL site, the loxP site, φpK02 telRL site, the FRT site, phiC31 attP site and the λ attP site.]

[4. The system of claim 3, wherein the vector comprises each of said target binding sequences.]

[5. The system of claim 3, wherein the vector comprises the Tel recombinase pal site and the telRL, loxP and FRT recombinase target binding sequences integrated within the pal site.]

[6. The system of claim 1, wherein the recombinase is selected from telN and tel, the vector incorporates the target binding sequence for at least said recombinase and said system produces a linear covalently closed vector.]

[7. The system of claim 1, wherein the recombinase is selected from cre and flp, the vector incorporates the target binding sequence for at least said recombinase and said system produces a circular covalently closed vector.]

[8. An expression vector adapted to produce a bacterial sequence-free vector, said expression vector comprising an expression cassette, and a nucleic acid of interest flanked on either side by a target binding sequence for the Tel recombinase and integrated within non-binding regions of the Tel target binding sequence are target binding sequences for one or more additional recombinases, wherein the nucleic acid of interest encodes a nuclease genome editing system.]

[9. The vector of claim 8, wherein the one or more additional target binding sequences are selected from the group consisting of telRL site, the loxP site, □K02 telRL site, the FRT site, phiC31 attP site and the λ attP site.]

[10. The vector of claim 9, comprising each of said target binding sequences.]

[11. The vector of claim 8, comprising the Tel recombinase pal site and telRL, loxP and FRT recombinase target binding sequences integrated within the pal site.]

[12. A method of producing a linear or circular covalently closed vector comprising incubating a vector production system as defined in claim 1 under conditions suitable to permit expression of the first recombinase to result in a linear or circular covalently closed vector.]

[13. The system of claim 1, wherein the Tel recombinase target binding site is the phage PY54 Tel 142 base pair target binding site.]

[14. The system of claim 1, wherein the nuclease genome editing system is selected from the group consisting of a Clustered Regularly Interspaced Short Palindromic Repeats (CRISPR) nuclease system, a Transcription Activator-Like Effector Nuclease (TALEN) and a Zinc-Finger Nuclease (ZFN).]

[15. The system of claim 14, wherein the nuclease genome editing system is a CRISPR nuclease system comprising a Cas9 nuclease.]

[16. The vector of claim 8, wherein the nuclease genome editing system is selected from the group consisting of a Clustered Regularly Interspaced Short Palindromic Repeats (CRISPR) nuclease system, a Transcription Activator-Like Effector Nuclease (TALEN) and a Zinc-Finger Nuclease (ZFN).]

[17. The vector of claim 16, wherein the nuclease genome editing system is a CRISPR nuclease system comprising a Cas9 nuclease.]

[18. A vector production system comprising recombinant cells designed to encode at least a first recombinase under the control of an inducible promoter, wherein said cells comprise an expression vector adapted to produce a bacterial sequence-free vector, said expression vector comprising backbone sequence, an expression cassette, and a nucleic acid of interest flanked on either side by a target binding sequence for the Tel recombinase and integrated within non-binding regions of the Tel target binding sequence are target binding sequences for one or more additional recombinases, wherein the cells are genetically modified to encode a nuclease genome editing system adapted to cleave the expression vector at a site within the backbone sequence.]

[19. The vector production system as defined in claim 18, wherein the nuclease genome editing system is a CRISPR nuclease system comprising a Cas9 nuclease and gRNA, and the expression vector comprises a target sequence for the gRNA within the backbone sequence.]

*20. A method of producing a bacterial sequence-free vector having covalently closed ends comprising:*

*incubating a vector production system comprising recombinant cells designed to encode at least a first recombinase under control of an inducible promoter and to encode a nuclease genome editing system, under suitable conditions for expression of the first recombinase and the nuclease genome editing system,*

*wherein the cells comprise an expression vector for producing the bacterial sequence-free vector having covalently closed ends, the expression vector comprising:*

*a backbone sequence containing a cleavage site for the nuclease genome editing system,*

*an expression cassette comprising a nucleic acid sequence of interest,*

*a target sequence for the first recombinase flanking each side of the expression cassette, and*

*one or more additional target sequences for one or more additional recombinases integrated within non-binding regions of the target sequence for the first recombinase.*

*21. The method of claim 20, further comprising harvesting the bacterial sequence-free vector.*

*22. The method of claim 20, wherein the inducible promoter is thermally-regulated, chemically-regulated, IPTG regulated, glucose-regulated, arabinose inducible, T7 polymerase regulated, cold-shock inducible, pH inducible, or a combination thereof.*

*23. The method of claim 20, wherein the target sequence for the first recombinase and the one or more additional target sequences for the one or more additional recombinases are selected from the group consisting of the PY54 pal site, the N15 telRL site, the loxP site, the φK02 telRL site, the FRT site, the phiC31 attP site, and the λ attP site.*

*24. The method of claim 23, wherein the expression vector comprises each of the target sequences.*

*25. The method of claim 23, wherein the expression vector comprises the Tel recombinase pal site and the telRL, loxP, and FRT recombinase target sequences integrated within the pal site.*

*26. The method of claim 20, wherein the bacterial sequence-free vector is a linear covalently closed vector.*

*27. The method of claim 26, wherein the first recombinase is selected from telN and tel.*

*28. The method of claim 20, wherein the bacterial sequence-free vector is a circular covalently closed vector.*

*29. The method of claim 28, wherein the first recombinase is selected from cre and flp.*

*30. The method of claim 20, wherein the target sequence for the first recombinase is the phage PY54 Tel 142 base pair target site.*

*31. The method of claim 20, wherein the nuclease genome editing system is selected from the group consisting of a Clustered Regularly Interspaced Short Palindromic Repeats (CRISPR) nuclease system, a Transcription Activator-Like Effector Nuclease (TALEN), and a Zinc-Finger Nuclease (ZFN).*

*32. The method of claim 31, wherein the nuclease genome editing system is a CRISPR nuclease system comprising a Cas nuclease.*

*33. The method of claim 20, wherein the nucleic acid sequence of interest encodes a nuclease genome editing system that is selected from the group consisting of a Clustered Regularly Interspaced Short Palindromic Repeats (CRISPR) nuclease system, a Transcription Activator-Like Effector Nuclease (TALEN), and a Zinc-Finger Nuclease (ZFN).*

*34. The method of claim 33, wherein the nuclease genome editing system is a CRISPR nuclease system comprising a Cas nuclease.*

*35. The method of claim 20, wherein the expression vector further comprises at least one enhancer sequence flanking each side of the target sequence for the first recombinase to facilitate nuclear uptake and enhance transfection efficiency of the bacterial sequence-free vector and expression of the nucleic acid sequence of interest.*

*36. The method of claim 35, wherein the at least one enhancer sequence is a SV40 enhancer sequence.*

*37. The method of claim 35, wherein the system comprises at least two enhancer sequences flanking each side of the target sequence for the first recombinase.*

*38. The method of claim 37, wherein the at least two enhancer sequences are SV40 enhancer sequences.*

*39. The method of claim 20, wherein the target sequence for the first recombinase and the one or more additional target sequences for the one or more additional recombinases have a total base pair length of less than or equal to 142 base pairs.*

*40. The method of claim 20, wherein the one or more additional target sequences for the one or more additional recombinases is at least five additional target sequences for at least five additional recombinases.*

*41. The method of claim 40, wherein the target sequence for the first recombinase and the at least five target sequences for the at least five additional recombinases have a total base pair length of less than or equal to 300 base pairs.*

* * * * *